United States Patent
Mitsialis et al.

(10) Patent No.: US 10,624,929 B2
(45) Date of Patent: Apr. 21, 2020

(54) METHODS AND COMPOSITIONS RELATING TO EXOSOMES

(71) Applicant: Children's Medical Center Corporation, Boston, MA (US)

(72) Inventors: S. Alexander Mitsialis, Newton, MA (US); Stella Kourembanas, Newton, MA (US); Konstantinos Sdrimas, Jamaica Plain, MA (US)

(73) Assignee: Children's Medical Center Corporation, Boston, MA (US)

( * ) Notice: Subject to any disclaimer, the term of this patent is extended or adjusted under 35 U.S.C. 154(b) by 360 days.

(21) Appl. No.: 15/312,047

(22) PCT Filed: May 15, 2015

(86) PCT No.: PCT/US2015/031008
§ 371 (c)(1),
(2) Date: Nov. 17, 2016

(87) PCT Pub. No.: WO2015/179227
PCT Pub. Date: Nov. 26, 2015

(65) Prior Publication Data
US 2017/0258840 A1    Sep. 14, 2017

Related U.S. Application Data

(60) Provisional application No. 61/994,974, filed on May 18, 2014.

(51) Int. Cl.
| | |
|---|---|
| *A61K 35/28* | (2015.01) |
| *A61K 35/51* | (2015.01) |
| *C12N 5/0775* | (2010.01) |
| *A61K 35/35* | (2015.01) |
| *A61K 35/15* | (2015.01) |
| *A61K 35/12* | (2015.01) |

(52) U.S. Cl.
CPC .............. *A61K 35/28* (2013.01); *A61K 35/12* (2013.01); *A61K 35/15* (2013.01); *A61K 35/35* (2013.01); *A61K 35/51* (2013.01); *C12N 5/0668* (2013.01)

(58) Field of Classification Search
CPC ........ A61K 35/15; A61K 35/28; A61K 35/12; A61K 35/51; A61K 35/35; C12N 5/0668
See application file for complete search history.

(56) References Cited

U.S. PATENT DOCUMENTS

| | | |
|---|---|---|
| 6,685,911 B1 | 2/2004 | Zitvogel et al. |
| 8,476,017 B2 | 7/2013 | Pietrzkowski |
| 9,901,600 B2 | 2/2018 | Mitsialis et al. |
| 2004/0214783 A1 | 10/2004 | Terman |
| 2006/0286089 A1 | 12/2006 | Berenson et al. |
| 2011/0003008 A1 | 1/2011 | Lim |
| 2013/0143314 A1 | 6/2013 | Shiels et al. |
| 2014/0065240 A1 | 3/2014 | Mitsialis et al. |
| 2015/0190430 A1 | 7/2015 | Lim |
| 2016/0190430 A1 | 6/2016 | Henning et al. |
| 2016/0220613 A1 | 8/2016 | Lim |
| 2018/0221412 A1 | 8/2018 | Mitsialis et al. |

FOREIGN PATENT DOCUMENTS

| | | |
|---|---|---|
| CN | 101890050 A | 11/2010 |
| JP | 2008-525490 A | 7/2008 |
| JP | 2014-507482 A | 3/2014 |
| JP | 2016-507550 A | 3/2016 |
| KR | 10-2010-0122087 | 11/2010 |
| KR | 20120002361 A | 1/2012 |
| WO | WO 2006/071796 A2 | 7/2006 |
| WO | WO 2007/027156 A1 | 3/2007 |
| WO | WO 2008/020815 A1 | 2/2008 |
| WO | WO 2008/060788 A2 | 5/2008 |
| WO | WO 2009/105044 A1 | 8/2009 |
| WO | WO 2011/010966 A1 | 1/2011 |

(Continued)

OTHER PUBLICATIONS

Strauss K. et al., "Exosome Secretion Ameliorates Lysosomal Storage of Cholesterol in Niemann-Pick Type C Disease", The Journal of Biological Chemistry, Aug. 10, 2010, vol. 285, No. 34, pp. 26279-26288. (Year: 2010).*
Bobrie A. et al., "Diverse subpopulations of vesicles secreted by different intracellular mechanisms are present in exosome preparations obtained by differential ultracentrifugation", Journal of Extracellular Vesicles, 2012, vol. 1, pp. 18397, Total pp. 1-11. (Year: 2012).*
Partial Supplementary European Search Report for European Application No. 15796048.5 dated Dec. 13, 2017.

(Continued)

*Primary Examiner* — Satyendra K Singh
(74) *Attorney, Agent, or Firm* — Wolf, Greenfield & Sacks, P.C.

(57) ABSTRACT

The disclosure provides compositions comprising exosome subpopulations, and methods of their use in subjects having certain disorders including lung disorders, cardiovascular disorders, renal disorders and ischemic neural disorders. The disclosure provides compositions comprising exosomes and methods of use thereof in the treatment and/or prevention of various diseases or disorders. 25 Accordingly, one aspect of the disclosure provides an isolated exosome. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, 30 the isolated exosome comprises 2, 3, 4, 5, 6, 7 or 8 markers selected from the group consisting of ALIX, TSG101, TGFBR2, SMAD1, SMAD2, SMAD3>SMAD5 and CD105.

14 Claims, 9 Drawing Sheets

(56) References Cited

FOREIGN PATENT DOCUMENTS

| WO | WO 2011/053257 A2 | 5/2011 |
|---|---|---|
| WO | WO 2012/115885 A1 | 8/2012 |
| WO | WO 2013/150303 A1 | 10/2013 |
| WO | WO 2014/028763 A1 | 2/2014 |
| WO | WO 2014/125277 A1 | 8/2014 |
| WO | WO 2015/179227 A1 | 11/2015 |

OTHER PUBLICATIONS

Tauro et al., Oncogenic H-ras reprograms Madin-Darby canine kidney (MDCK) cell-derived exosomal proteins following epithelial-mesenchymal transition. Mol Cell Proteomics. Aug. 2013;12(8):2148-59.doi: 10.1074/mcp.M112.027086. Epub May 3, 2013.

Aslam et al., Bone marrow stromal cells attenuate lung injury in a murine model of neonatal chronic lung disease. Am J Respir Crit Care Med. Dec. 1, 2009;180(11):1122-30. Epub Aug. 27, 2009.

Bonfield et al., Adult mesenchymal stem cells: an innovative therapeutic for lung diseases. Discov Med. Apr. 2010;9(47):337-45. Retrieved from the internet May 25, 2012 viahttp://www.discoverymedicine/com/Tracey-L-Bonfield/2010/04/15/adult-mesenchymal-stem-cells-an-innovative-therapeutic-for-lung-diseases/.

Bruno et al., Mesenchymal stem cell-derived microvesicles protect against acute tubular injury. J Am Soc Nephrol. May 2009;20(5):1053-67. doi: 10.1681/ASN.2008070798. Epub Apr. 23, 2009.

Choi et al., Proteomic analysis of microvesicles derived from human colorectal cancer ascites. Proteomics. Jul. 2011;11(13):2745-51. doi: 10.1002/pmic.201100022. Epub Jun. 1, 2011.

Gallo et al., The majority of microRNAs detectable in serum and saliva is concentrated in exosomes. PLoS One. 2012;7(3):e30679. doi: 10.1371/journal.pone.0030679. Epub Mar. 9, 2012.

Gotts et al., Mesenchymal stem cells and acute lung injury. Crit Care Clin. Jul. 2011;27(3):719-33. Epub May 23, 2011.

Gupta et al., Intrapulmonary delivery of bone marrow-derived mesenchymal stem cells improves survival and attenuates endotoxin-induced acute lung injury in mice. J Immunol. Aug. 1, 2007;179(3):1855-63.

Katsha et al., Paracrine factors of multipotent stromal cells ameliorate lung injury in an elastase-induced emphysema model. Mol Ther. Jan. 2011;19(1):196-203. Epub Sep. 14, 2010.

Lai et al., Exosome secreted by MSC reduces myocardial ischemia/reperfusion injury. Stem Cell Res. May 2010;4(3):214-22. doi: 10.1016/j.scr.2009.12.003. Epub Jan. 4, 2010.

Lee et al., Exosomes Mediate the Cytoprotective Effects of Bone Marrow-Derived Stromal Cells (MSCs) on the Hypoxic Lung. American Thoracic Society International Conference Abstracts. May 13-18, 2011. Abstract 21620.

Lee et al., Intravenous hMSCs improve myocardial infarction in mice because cells embolized in lung are activated to secrete the anti-inflammatory protein TSG-6. Cell Stem Cell. Jul. 2, 2009;5(1):54-63. doi: 10.1016/j.stem.2009.05.003.

Matthay et al., Mesenchymal stem cells for acute lung injury: preclinical evidence. Crit Care Med. Oct. 2010;38(10 Suppl):S569-73.

Mei et al., Prevention of LPS-induced acute lung injury in mice by mesenchymal stem cells overexpressing angiopoietin 1. PLoS Med. Sep. 2007;4(9):e269, pp. 1525-1537.

Musina et al., Comparison of mesenchymal stem cells obtained from different human tissues. Bull Exp Biol Med. Apr. 2005;139(4):504-9.

Ortiz et al., Mesenchymal stem cell engraftment in lung is enhanced in response to bleomycin exposure and ameliorates its fibrotic effects. Proc Natl Acad Sci U S A. Jul. 8, 2003;100(14):8407-11. Epub Jun. 18, 2003.

Paine et al., Dentin sialoprotein and dentin phosphoprotein overexpression during amelogenesis. J Biol Chem. Sep. 9, 2005;280(36):31991-8. Epub Jul. 13, 2005.

Patel et al., Mesenchymal stem cells attenuate hypoxic pulmonary vasoconstriction by a paracrine mechanism. J Surg Res. Dec. 2007;143(2):281-5. Epub Sep. 14, 2007.

Rojas et al., Bone marrow-derived mesenchymal stem cells in repair of the injured lung. Am J Respir Cell Mol Biol. Aug. 2005;33(2):145-52. Epub May 12, 2005.

Spees et al., Bone marrow progenitor cells contribute to repair and remodeling of the lung and heart in a rat model of progressive pulmonary hypertension. FASEB J. Apr. 2008;22(4):1226-36.

Van Haaften et al., Airway delivery of mesenchymal stem cells prevents arrested alveolar growth in neonatal lung injury in rats. Am J Respir Crit Care Med. Dec. 1, 2009;180(11):1131-42. Epub Aug. 27, 2009.

Weiss et al., Embryonic stem cells and repair of lung injury. Mol Ther. Mar. 2010;18(3):460-1.

Xu et al., Prevention of endotoxin-induced systemic response by bone marrow-derived mesenchymal stem cells in mice. Am J Physiol Lung Cell Mol Physiol. Jul. 2007;293(1):L131-41. Epub Apr. 6, 2007.

Edgar, Q&A: What are exosomes, exactly? BMS Biology, 2016; vol. 14(46):1-7. doi: 10.1186/s12915-016-0268-z.

Ji et al., Proteome profiling of exosomes derived from human primary and metastatic colorectal cancer cells reveal differential expression of key metastatic factors and signal transduction components. Proteomics. May 2013;13(10-11):1672-86. doi: 10.1002/pmic.201200562.

Jørgensen et al., Extracellular Vesicle (EV) Array: microarray capturing of exosomes and other extracellular vesicles for multiplexed phenotyping. J Extracell Vesicles. Jun. 18, 2013;2. doi: 10.3402/jev.v2i0.20920. eCollection 2013.

Kalra et al., Comparative proteomics evaluation of plasma exosome isolation techniques and assessment of the stability of exosomes in normal human blood plasma. Proteomics. Nov. 2013;13(22):3354-64. doi: 10.1002/pmic.201300282. Epub Oct. 18, 2013.

Mathivanan et al., Exosomes: extracellular organelles important in intercellular communication. J Proteomics. Sep. 10, 2010;73(10):1907-20. doi: 10.1016/j.jprot.2010.06.006. Epub Jul. 1, 2010.

Simpson et al., Exosomes: proteomic insights and diagnostic potential. Expert Rev Proteomics. Jun. 2009;6(3):267-83. doi: 10.1586/epr.09.17.

Collino et al., Exosome and Microvesicle-Enriched Fractions Isolated from Mesenchymal Stem Cells by Gradient Separation Showed Different Molecular Signatures and Functions on Renal Tubular Epithelial Cells. Stem Cell Rev. Apr. 2017;13(2):226-243. doi: 10.1007/s12015-016-9713-1.

Donnarumma et al., Cancer-associated fibroblasts release exosomal microRNAs that dictate an aggressive phenotype in breast cancer. Oncotarget. Mar. 21, 2017;8(12):19592-19608.

Lee et al., Exosomes mediate the cytoprotective action of mesenchymal stromal cells on hypoxia-induced pulmonary hypertension. Circulation. Nov. 27, 2012;126(22):2601-11.

Long et al., Intranasal MSC-derived A1-exosomes ease inflammation, and prevent abnormal neurogenesis and memory dysfunction after status epilepticus. Proc Natl Acad Sci U S A. Apr. 25, 2017;114(17):E3536-E3545. doi: 10.1073/pnas.1703920114.

Lou et al., Mesenchymal stem cell-derived exosomes as a new therapeutic strategy for liver diseases. Exp Mol Med. Jun. 16, 2017;49(6):e346. doi: 10.1038/emm.2017.63.

Tannetta et al., Characterization of syncytiotrophoblast vesicles in normal pregnancy and preeclampsia: expression of Flt-1 and endoglin. PLoS One. 2013;8(2):e56754. doi: 10.1371/journal.pone.0056754.

\* cited by examiner

WJ-MSCs grown in 3D culture produce predominantly *a*-MEX

Hanging drop culture

Clone D                Clone C

Addition of TGFβ1 to monolayer MSC cultures enhances production of a-MEX

METHODS AND COMPOSITIONS RELATING TO EXOSOMES

RELATED APPLICATIONS

This application is a national stage filing under 35 U.S.C. 371 of International Application PCT/US2015/031008, filed May 15, 2015, which claims the benefit under 35 U.S.C. § 119(e) of U.S. Provisional Patent Application filed May 18, 2014, entitled "METHODS AND COMPOSITIONS RELATING TO EXOSOMES", Ser. No. 61/994,974, the contents of which are incorporated by reference in their entirety. International Application PCT/US2015/031008 was published under PCT Article 21(2) in English.

BACKGROUND OF INVENTION

Exosomes are cell-derived vesicles that are present in many and perhaps all biological fluids, including blood, urine, and conditioned media from cell cultures. The reported diameter of exosomes is typically between 30 and 100 nm, which, for comparison, is larger than LDL but significantly smaller than red blood cells. Exosomes are known to be released from cells when multivesicular bodies fuse with the plasma membrane or when they are released directly from the plasma membrane. It is becoming increasingly clear that exosomes have specialized functions and play a key role in, for example, coagulation, intercellular signaling, and waste management. Consequently, there is a growing interest in the clinical applications of exosomes, including synthetic exosomes which recapitulate aspects of cell-derived exosomes. Exosomes can potentially be used for prognosis, therapy, and biomarkers for health and disease.

SUMMARY OF INVENTION

The disclosure provides compositions comprising exosomes and methods of use thereof in the treatment and/or prevention of various diseases or disorders.

Accordingly, one aspect of the disclosure provides an isolated exosome. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, the isolated exosome comprises 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome comprises the markers ALIX, TSG101, TGFBR2, SMAD1, SMAD2, SMAD3, SMAD5 and CD105. In some embodiments, the isolated exosome does not comprise 2, 3, 4, 5, 6 or 7 markers selected from the group consisting of FLOT1, CD9, CD81, CAV1, EGFR, AKT1 and AKT2. In some embodiments, the isolated exosome does not comprise the markers FLOT1, CD9, CD81, CAV1, EGFR, AKT1 and AKT2. In some embodiments, the isolated exosome has spherical morphology and appears radiolucent upon negative staining in transmission electron microscopy, and/or the isolated exosome does not have a cup shape morphology in negative staining transmission electron microscopy. The isolated exosome may have a diameter of about 10-150 nm. In some embodiments, the isolated exosome has a diameter of about 30-100 nm. In some embodiments, the isolated exosome is isolated from a mesenchymal stem cell (MSC), fibroblast, or macrophage. In some embodiments, the MSC, fibroblast, or macrophage is a human MSC, human fibroblast, or human macrophage. In some embodiments, the MSC is isolated from Wharton's jelly, umbilical cord blood, placenta, peripheral blood, bone marrow, or adipose tissue. In some embodiments, the isolated exosome is comprised in a composition. In some embodiments, the composition is a pharmaceutical composition.

According to another aspect of the disclosure, an isolated exosome is provided. In some embodiments, the isolated exosome comprises one or more markers selected from the group consisting of FLOT1, CD9, CD81, CAV1, EGFR, AKT1 and AKT2, and/or the isolated exosome does not comprise one or markers selected from the group consisting of ALIX, TSG101, TGFBR2, SMAD1, SMAD2, SMAD3, SMAD5 and CD105. In some embodiments, the isolated exosome comprises 2, 3, 4, 5, 6 or 7 markers selected from the group consisting of FLOT1, CD9, CD81, CAV1, EGFR, AKT1 and AKT2. In some embodiments, the isolated exosome comprises the markers FLOT1, CD9, CD81, CAV1, EGFR, and AKT1 and AKT2. In some embodiments, the isolated exosome does not comprise 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome does not comprise the markers ALIX, TSG101, TGFBR2, SMAD1, SMAD2, SMAD3, SMAD5, and CD105. In some embodiments, the isolated exosome has cup shaped morphology in negative staining transmission electron microscopy and/or does not have a spherical morphology in negative staining transmission electron microscopy. In some embodiments, the isolated exosome has a diameter of about 10-250 nm. In some embodiments, the isolated exosome has a diameter of about 30-200 nm.

According to another aspect, a method for treating a lung disorder, a cardiovascular disorder, a renal disorder, or an ischemic neural disorder is provided. In some embodiments, the method comprises administering to a subject having or at risk of having a lung disorder, a cardiovascular disorder, a renal disorder, or an ischemic neural disorder a therapeutically effective amount of an isolated exosome. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, the isolated exosome comprises 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome comprises the markers ALIX, TSG101, TGFBR2, SMAD1, SMAD2, SMAD3, SMAD5 and CD105. In some embodiments, the isolated exosome does not comprise 2, 3, 4, 5, 6 or 7 markers selected from the group consisting of FLOT1, CD9, CD81, CAV1, EGFR, AKT1 and AKT2. In some embodiments, the isolated exosome does not comprise the markers FLOT1, CD9, CD81, CAV1, EGFR, AKT1 and AKT2. In some embodiments, the isolated exosome has spherical morphology and appears radiolucent upon negative staining in transmission electron microscopy and/or the isolated exosome does not have a cup shape morphology in negative staining transmission electron microscopy. In some embodiments, the isolated exosome has a diameter of about 10-150 nm. In some embodiments, the isolated exosome has a diameter of about 30-100 nm. In some embodiments, the isolated exosome is isolated from a mesenchymal stem cell (MSC), fibroblast, or macrophage. In some embodiments, the MSC, fibroblast, or macrophage is a human MSC, human fibroblast, or human macrophage. In some embodiments, the MSC is isolated from Wharton's jelly, umbilical cord blood, placenta, peripheral blood, bone marrow, or adipose tissue. In some embodiments, the lung disorder being treated is inflammatory lung disease, lung vascular disease, or acute lung injury. In some embodiments, the inflammatory lung disease is hypoxia-induced lung inflammation, pulmonary hypertension, asthma, bronchopulmonary dysplasia (BPD), allergy, or idiopathic pulmonary fibrosis. In some embodiments, the acute lung injury is associated with sepsis or is ventilator-induced acute respiratory distress syndrome (ARDS). In some embodiments, a cardiovascular disorder being treated according to the method is myocardial infarction, cardiovascular disease, hypertension, atherosclerosis, or heart failure. In some embodiments involving the treatment of renal disorders, the renal disorder is ischemic renal injury, acute renal failure, or renal fibrosis. In embodiments of the method involving the treatment of ischemic neural disorders, the disorder is hypoxic ischemic encephalopathy or ischemic stroke.

According to yet another aspect of the disclosure, use of an isolated exosome for treating a lung disorder, a cardiovascular disorder, a renal disorder, or an ischemic neural disorder is provided. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, the isolated exosome comprises 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome the markers ALIX, TSG101, TGFBR2, SMAD1, SMAD2, SMAD3, SMAD5 and CD105. In some embodiments, the isolated exosome does not comprise 2, 3, 4, 5, 6 or 7 markers selected from the group consisting of FLOT1, CD9, CD81, CAV1, EGFR, AKT1 and AKT2. In some embodiments, the isolated exosome does not comprise the markers FLOT1, CD9, CD81, CAV1, EGFR, AKT1 and AKT2. In some embodiments, the isolated exosome has spherical morphology and appears radiolucent upon negative staining in transmission electron microscopy and/or the isolated exosome does not have a cup shape morphology in negative staining transmission electron microscopy. In some embodiments, the isolated exosome has a diameter of about 10-150 nm. In some embodiments, the isolated exosome has a diameter of about 30-100 nm. In some embodiments, the isolated exosome is isolated from a mesenchymal stem cell (MSC), fibroblast, or macrophage. In some embodiments, the MSC, fibroblast, or macrophage is a human MSC, human fibroblast, or human macrophage. In some embodiments, the MSC is isolated from Wharton's jelly, umbilical cord blood, placenta, peripheral blood, bone marrow, or adipose tissue. In some embodiments, the lung disorder is inflammatory lung disease, lung vascular disease, or acute lung injury. In some embodiments, the inflammatory lung disease is hypoxia-induced lung inflammation, pulmonary hypertension, asthma, bronchopulmonary dysplasia (BPD), allergy, or idiopathic pulmonary fibrosis. In some embodiments, the acute lung injury is associated with sepsis or is ventilator-induced acute respiratory distress syndrome (ARDS). In some embodiments, the cardiovascular disorder is myocardial infarction, cardiovascular disease, hypertension, atherosclerosis, or heart failure. In some embodiments, the renal disorder is ischemic renal injury, acute renal failure, or renal fibrosis. In some embodiments, the ischemic neural disorder is hypoxic ischemic encephalopathy or ischemic stroke.

According to another aspect, use of an isolated exosome in the manufacture of a medicament for treating a lung disorder, a cardiovascular disorder, a renal disorder, or an ischemic neural disorder is provided. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, the isolated exosome comprises 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome comprises the markers ALIX, TSG101, TGFBR2, SMAD1, SMAD2, SMAD3, SMAD5 and CD105. In some embodiments, the isolated exosome does not comprise 2, 3, 4, 5, 6 or 7 markers selected from the group consisting of FLOT1, CD9, CD81, CAV1, EGFR, AKT1 and AKT2. In some embodiments, the isolated exosome does not comprise the markers FLOT1, CD9, CD81, CAV1, EGFR, AKT1 and AKT2. In some embodiments, the isolated exosome has spherical morphology and appears radiolucent upon negative staining in transmission electron microscopy; and/or the isolated exosome does not have a cup shape morphology in negative staining transmission electron microscopy. In some embodiments, the isolated exosome has a diameter of about 10-150 nm. In some embodiments, the isolated exosome has a diameter of about 30-100 nm. In some embodiments, the isolated exosome is isolated from a mesenchymal stem cell (MSC), fibroblast, or macrophage. In some embodiments, the MSC, fibroblast, or macrophage is a human MSC, human fibroblast, or human macrophage. In some embodiments, the MSC is isolated from Wharton's jelly, umbilical cord blood, placenta, peripheral blood, bone marrow, or adipose tissue. In some embodiments involving the use of exosomes for the manufacture of a medicament for the treatment of lung disorders, the disorder is inflammatory lung disease, lung vascular disease, or acute lung injury. In some embodiments, the inflammatory lung disease is hypoxia-induced lung inflammation, pulmonary hypertension, asthma, bronchopulmonary dysplasia (BPD), allergy, or idiopathic pulmonary fibrosis. In some embodiments, the acute lung injury is associated with sepsis or is ventilator-induced acute respiratory distress syndrome (ARDS). In some embodiments, use of the exosome for the manufacture of medicament for the treatment of a cardiovascular disorder is provided, the disorder being myocardial infarction, cardiovascular disease, hypertension, atherosclerosis, or heart failure. In some embodiments involving the use of exosomes for the manufacture of a medicament for the treatment of renal disorders, the renal disorder is ischemic renal injury, acute renal failure, or renal fibrosis. In some embodiments involving the use of exosomes for the manufacture of a medicament for the treatment of ischemic neural disorders, the disorder is hypoxic ischemic encephalopathy or ischemic stroke.

According to yet another aspect of the disclosure, a method for producing an exosome(s) is provided. In some embodiments, the method comprises culturing a cell so as to produce conditioned media and isolating the exosome from the conditioned media. In some embodiments, the isolated exosome comprises one or more markers selected from the group consisting of ALIX, TSG101, TGFBR2, SMAD1, SMAD2, SMAD3, SMAD5 and CD105, and/or the isolated exosome does not comprise one or more markers selected from the group consisting of FLOT1, CD9, CD81, CAV1, EGFR, AKT1 and AKT2. In some embodiments, the isolated exosome comprises 2, 3, 4, 5, 6, 7 or 8 markers selected from the group consisting of ALIX, TSG101, TGFBR2, SMAD1, SMAD2, SMAD3, SMAD5 and CD105. In some embodiments, the isolated exosome the markers ALIX, TSG101, TGFBR2, SMAD1, SMAD2, SMAD3, SMAD5 and CD105. In some embodiments, the isolated exosome does not comprise 2, 3, 4, 5, 6 or 7 markers selected from the group consisting of FLOT1, CD9, CD81, CAV1, EGFR, AKT1 and AKT2. In some embodiments, the isolated exosome does not comprise the markers FLOT1, CD9, CD81, CAV1, EGFR, AKT1 and AKT2. In some embodiments, the isolated exosome has spherical morphology and appears radiolucent upon negative staining in transmission electron microscopy and/or the isolated exosome does not have a cup shape morphology in negative staining transmission electron microscopy. In some embodiments, the isolated exosome has a diameter of about 10-150 nm. In some embodiments, the isolated exosome has a diameter of about 30-100 nm. In some embodiments, the isolated exosome is isolated from a mesenchymal stem cell (MSC), fibroblast, or macrophage. In some embodiments, the MSC, fibroblast, or macrophage is a human MSC, human fibroblast, or human macrophage. In some embodiments, the MSC is isolated from Wharton's jelly, umbilical cord blood, placenta, peripheral blood, bone marrow, or adipose tissue. In some embodiments, the culturing involves two-dimensional (2D) or three-dimensional (3D) culturing. In some embodiments, the 3D culturing comprises hanging drop culturing, culturing on matrices, culturing on microcarriers, culturing on synthetic extracellular scaffolds, culturing on chitosan membranes, culturing under magnetic levitation, suspension culture in rotating bioreactors, or culturing under non-contact inhibition conditions. In some embodiments, the culturing comprises use of one or more growth factors selected from TGFβ superfamily (TGFβ1, Activins, BMPs, GDFs, GDNFs, Inhibins, Nodal, Lefty, MIS) EGF, PDGF, and FGF. In some embodiments, the method enhances the production of exosomes that comprise one or more markers selected from ALIX, TSG101, TGFBR2, SMAD1, SMAD2, SMAD3, SMAD5 and CD105 relative to exosomes that comprise one or more markers selected from the group consisting of FLOT1, CD9, CD81, CAV1, EGFR, AKT1 and AKT2. In some embodiments, the enhancement comprises a 1.5-fold, 2.0-fold, 2.5-fold, 3.0-fold, 3.5-fold, 4.0-fold, 4.5-fold, or 5.0-fold, 6.0-fold, 7.0-fold, 8.0-fold, 9.0-fold, or 10.0-fold or more increase in the production of exosomes that comprise one or more markers selected from ALIX, TSG101, TGFBR2, SMAD1, SMAD2, SMAD3, SMAD5 and CD105 relative to exosomes that comprise one or more markers selected from the group consisting of FLOT1, CD9, CD81, CAV1, EGFR, AKT1 and AKT2.

These and other aspects and embodiments of the disclosure will be described in greater detail herein.

DETAILED DESCRIPTION OF INVENTION

Figure 1A:
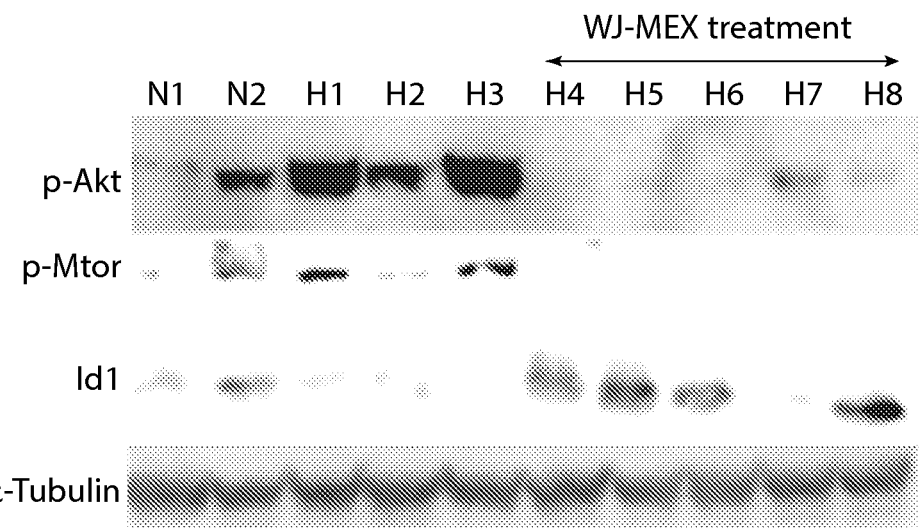
FIG. 1. Treatment of mice by I.V. injection of mesenchymal stem cell exosome (MEX) preparations down-regulates the hypoxic activation of signaling associated with vascular remodeling & pulmonary hypertension and ameliorates the hypoxia-induced lung inflammation. (A) Age-matched FVB/n mice were injected with human MEX (20 billion particles/mouse) and exposed to hypoxia for 2.5 days. Hypoxia-induced phosphorylation of AKT and its downstream target mTOR are reduced by MEX treatment. Lung protein levels of the Inhibitor of DNA-binding/differentiation protein ID1, a direct SMAD-targeted gene and downstream signal of BMPR2 are suppressed by hypoxia but increased with MEX. Alpha tubulin serves as normalizing control. (B) mRNA levels of CCL2, an early inflammatory marker, are suppressed with MEX treatment. RNA levels are normalized to RPS9.

The disclosure is based, in part, on the surprising finding that two types of exosomes are derived from cells such as mesenchymal stem cells, and the exosomes can be distinguished based on molecular markers, size, morphology, and function. For example, one of the two subpopulations comprises distinct markers and has therapeutic efficacy in the treatment of certain disorders, whereas the other subpopulation comprises a separate and distinct group of markers and lacks therapeutic efficacy in treating certain disorders.

The disclosure relates broadly to compositions of isolated exosomes and methods of their use in the treatment and/or prevention of certain diseases or disorders including but not limited to lung disorders, cardiovascular disorders, renal disorders, and ischemic neural disorders.

Exosomes and Exosome Preparation

The exosomes of the disclosure are membrane (e.g., lipid bilayer) vesicles that are released from cells such as mesenchymal stem cells (MSCs), fibroblasts, and macrophages. By electron microscopy, exosomes have typically been described as having a cup-shaped morphology. However, aspects of the present disclosure relate to the novel finding that some exosomes (e.g., those having therapeutic efficacy as described herein) within a given preparation display a spherical morphology as opposed to cup-shaped, and are also radiolucent (e.g., translucent) as determined by negative staining transmission electron microscopy. Exosomes sediment at about 100,000×g and have a buoyant density in sucrose of about 1.10 to about 1.21 g/ml. Exosomes may be referred to as microvesicles or nanovesicles.

Some aspects of the disclosure refer to isolated exosomes. As used herein, an isolated exosome is one which is physically separated from its natural environment. An isolated exosome may be physically separated, in whole or in part, from tissue or cells with which it naturally exists, including MSCs, fibroblasts, and macrophages. In some embodiments of the disclosure, a composition of isolated exosomes may be free of cells such as MSCs, fibroblasts, and macrophages, or it may be free or substantially free of conditioned media. Typically, the isolated exosomes are provided at a higher concentration than exosomes present in unmanipulated conditioned media.

Exosomes may be isolated from conditioned media from cultures of cells including, but not limited to, MSCs, fibroblasts, and macrophages. A method for harvest of exosomes from MSCs is provided in the Examples. Briefly, such method involves first culturing MSCs under standard conditions until they reach about 70% confluency, and then culturing the cells in a serum-free media for 24 hours, following which the conditioned media is collected and subjected to differential centrifugation at 400×g for 10 minutes and 12000×g for 10 minutes in order to remove cells and cellular debris. The clarified conditioned media is then concentrated by ultrafiltration using a 100 kDa MWCO filter (Millipore), and then centrifuged again at 12000×g for 10 minutes. Exosomes are then isolated using size exclusion chromatography by loading the concentrated conditioned media on a PBS-equilibrated Chroma S-200 column (Clontech), eluting with PBS, and collecting fractions of 350-550 microliters. Fractions containing exosomes are identified and potentially pooled. Protein concentration is measured using a standard Bradford assay (Bio-Rad). Aliquots of the enriched exosome preparations can be stored at −80° C.

Exosomes can also be purified by ultracentrifugation of clarified conditioned media at 100,000×g. They can also be purified by ultracentrifugation into a sucrose cushion. GMP methods for exosome purification from dendritic cells have been described in J Immunol Methods. 2002; 270:211-226.

Exosomes can also be purified by differential filtration, through nylon membrane filters of defined pore size. A first filtration though a large pore size will retain cellular fragments and debris. A subsequent filtration through a smaller pore size will retain exosomes and purify them from smaller size contaminants.

In some embodiments, the exosomes are fractionated into the two subpopulations enriched for certain markers described herein. Methods for fractionating the two subpopulations are described in the Examples, and include, for example, velocity ultracentrifugation in step gradients of sucrose (5%-60%), iodixanol (Optiprep™, 0%-60%) or similar isolation media.

In some embodiments, the disclosure provides two distinct types of exosomes that are distinguished based on molecular markers, size, morphology, and function. The two distinct types are referred to as the "a-type" and "f-type" throughout the disclosure, and when derived from MSCs are interchangeably referred to as "a-MEX" (for "a" type MSC derived exosome) or "f-MEX" (for "f" type MSC derived exosome). Surprisingly, it is the a-type exosomes that exhibit therapeutic efficacy in the treatment of certain disorders, for example lung disorders; whereas the f-type exosomes do not exhibit any therapeutic efficacy in the same treatment paradigms. While not being bound by any particular mechanism, it is believed that the molecular signature of each type of exosome specifies its effect or function on target cells or tissues.

For example, in some embodiments, isolated exosomes of the a-type comprise one or more markers (e.g., proteins) selected from the group consisting of ALIX (also known as "programmed cell death 6 interacting protein" or PDCD6IP; HomoloGene:22614; e.g., NCBI Reference Sequence: NP_001155901.1), TSG101 (tumor susceptibility gene 101; HomoloGene:4584; e.g., NCBI Reference Sequence: NP_006283.1), TGFBR2 (transforming growth factor, beta receptor II; HomoloGene:2435; e.g., NCBI Reference Sequence: NP_001020018.1), SMAD1 (SMAD family member 1; HomoloGene:21196; e.g., NCBI Reference Sequence: NP_001003688.1), SMAD2 (SMAD family member 2; HomoloGene:21197; e.g., NCBI Reference Sequence: NP_001003652.1), SMAD3 (SMAD family member 3; HomoloGene:55937; e.g., NCBI Reference Sequence: NP_001138574.1), SMAD5 (SMAD family member 5; HomoloGene:4313; e.g., NCBI Reference Sequence: NP_001001419.1) and CD105 (also known as Endoglin or ENG; HomoloGene:92; e.g., NCBI Reference Sequence: NP_000109.1; NP_001108225.1; NP_001265067.1). In some embodiments, the a-type comprises 2, 3, 4, 5, 6, 7, or 8 of these markers. In some embodiments, when an exosome "comprises" a particular marker, it is meant that the exosome contains detectable levels (e.g., as determined by Western blotting) of the marker and/or levels sufficient to elicit a certain response in a target cell or tissue or elicit a certain response in a subject in the context of methods of treatment as described herein. Some of these markers (e.g., proteins) which may be found in a-type exosomes comprise part of the TGF/BMP superfamily of growth factors, which are believed to contribute to their function and therapeutic effects. In some embodiments, isolated exosomes of the a-type do not comprise one or more markers selected from the group consisting of FLOT1 (flotillin 1; HomoloGene:31337; e.g., NCBI Reference Sequence: NP_005794.1), CD9 (CD9 molecule; HomoloGene:20420; e.g., NCBI Reference Sequence: NP_001760.1), CD81 (CD81 molecule; HomoloGene: 20915; e.g., NCBI Reference Sequence: NP_004347.1), CAV1 (caveolin 1; HomoloGene:1330; e.g., NCBI Reference Sequence: NP_001166366.1), EGFR (epidermal growth factor receptor; HomoloGene:74545; e.g., NCBI Reference Sequence: NP_005219.2; NP_958439.1; NP_958440.1; NP_958441.1), AKT1 (v-akt murine thymoma viral oncogene homolog 1; HomoloGene:3785; e.g., NCBI Reference Sequence: NP_001014431.1) and AKT2 (v-akt murine thymoma viral oncogene homolog 2; HomoloGene:48773; e.g., NCBI Reference Sequence: NP_001229956.1). In some embodiments, the a-type does not comprise 2, 3, 4, 5, 6, or 7 of these markers. In some embodiments, when an exosome "does not comprise" a particular marker, it is meant that the exosome contains none of or only insignificant amounts of the particular marker. For example, an insignificant amount may be an amount that is undetectable, or an amount that is detectable at only trace amounts.

In some embodiments, an a-type exosome may be distinguished from an f-type exosome based on morphology. Exosomes have been typically described as having a cup-shaped morphology. Surprisingly, the present disclosure provides exosomes (the a-type) having a spherical as opposed to a cup-shaped morphology. Methods for assessing exosome morphology are known in the art, and include transmission electron microscopy and negative staining in transmission electron microscopy. Further, a-type exosomes were found to be radiolucent (e.g., translucent) using negative staining in transmission electron microscopy. Conversely, the f-type exosomes display cup-shaped morphology and are not radiolucent as determined by negative staining in transmission electron microscopy.

In some embodiments, the a-type exosomes are distinguished from f-type exosomes based on size. For example, in some embodiments, a-type exosomes have a diameter of about 10-150 nm, about 20-120 nm, or about 30-100 nm.

In other aspects, the disclosure provides isolated exosomes of the f-type. In some embodiments, isolated exosomes of the f-type comprise one or more markers (e.g., proteins) selected from the group consisting of FLOT1, CD9, CD81, CAV1, EGFR, AKT1 and AKT2. In some embodiments, isolated exosomes of the f-type comprise 2, 3, 4, 5, 6, or 7 of these markers. In some embodiments, when an exosome "comprises" a particular marker, it is meant that the exosome contains detectable levels (e.g., as determined by Western blotting) of the marker and/or levels sufficient to elicit a certain response in a target cell or tissue or elicit a certain response in a subject in the context of methods of treatment as described herein. Some of these markers (e.g., proteins) which may be found in f-type exosomes comprise part of the FGF/PDGF superfamily of growth factors. The FGF/PDGF signaling pathway is involved in angiogenesis. Accordingly, f-type exosomes (e.g., compositions thereof) are believed to be useful for augmenting angiogenesis. In some embodiments, isolated f-type exosomes do not comprise one or markers selected from the group consisting of ALIX, TSG101, TGFBR2, SMAD1, SMAD2, SMAD3, SMAD5 and CD105. In some embodiments, f-type exosomes do not comprise 2, 3, 4, 5, 6, 7, or 8 of these markers. In some embodiments, when an exosome "does not comprise" a particular marker, it is meant that the exosome contains none of or only insignificant amounts of the particular marker. For example, an insignificant amount may be an amount that is undetectable, or an amount that is detectable at only trace amounts.

As described above and in the Examples, f-type exosomes display cup-shaped morphology as determined by negative staining transmission electron microscopy. In some embodiments, f-type exosomes have a diameter of about 10-250 nm, about 20-230 nm, or about 30-200 nm. In some embodiments, f-type exosomes have a diameter of no less than 100 nm.

Exosomes, including both a-type and f-type exosomes, are produced by a number of different cell types, including, but not limited to, MSCs, fibroblasts, and macrophages. Methods for obtaining such cells are well known in the art. Sources of MSCs are described in more detail herein.

The disclosure also contemplates the use of synthetic exosomes having some or all the characteristics of the isolated exosomes described herein. These synthetic exosomes would be synthesized in vitro (rather than derived and isolated from cells or conditioned media). They may be synthetic liposomes having one or more, including 2, 3, 4, 5, 6, 7, 8 or more of the proteins provided herein. They may or may not comprise nucleic acids that encode one or more, including 2, 3, 4, 5, 6, 7, 8 or more of these proteins. Liposome synthesis is known in the art, and liposomes may be purchased from commercial sources. It is to be understood that the various compositions, formulations, methods and uses described herein relating to exosomes derived and isolated from cells (or conditioned media from cells) such as MSCs, fibroblasts, or macrophages are also contemplated in the context of synthetic exosomes.

The disclosure contemplates immediate use of exosomes or alternatively short- and/or long-term storage of exosomes, for example, in a cryopreserved state prior to use. Proteinase inhibitors are typically included in freezing media as they provide exosome integrity during long-term storage. Freezing at −20° C. is not preferable since it is associated with increased loss of exosome activity. Quick freezing at −80° C. is more preferred as it preserves activity. (See for example Kidney International (2006) 69, 1471-1476.) Additives to the freezing media may be used in order to enhance preservation of exosome biological activity. Such additives will be similar to the ones used for cryopreservation of intact cells and may include, but are not limited to DMSO, glycerol and polyethylene glycol.

Cells

A mesenchymal stem cell (MSC) is a progenitor cell having the capacity to differentiate into neuronal cells, adipocytes, chondrocytes, osteoblasts, myocytes, cardiac tissue, and other endothelial and epithelial cells. (See for example Wang, Stem Cells 2004; 22(7); 1330-7; McElreavey; 1991 Biochem Soc Trans (1); 29s; Takechi, Placenta 1993 March/April; 14 (2); 235-45; Takechi, 1993; Kobayashi; Early Human Development; 1998; Jul. 10; 51 (3); 223-33; Yen; Stem Cells; 2005; 23 (1) 3-9.) These cells may be defined phenotypically by gene or protein expression. These cells have been characterized to express (and thus be positive for) one or more of CD13, CD29, CD44, CD49a, b, c, e, f, CD51, CD54, CD58, CD71, CD73, CD90, CD102, CD105, CD106, CDw119, CD120a, CD120b, CD123, CD124, CD126, CD127, CD140a, CD166, P75, TGF-bIR, TGF-bIIR, HLA-A, B, C, SSEA-3, SSEA-4, D7 and PD-L1. These cells have also been characterized as not expressing (and thus being negative for) CD3, CD5, CD6, CD9, CD10, CD11a, CD14, CD15, CD18, CD21, CD25, CD31, CD34, CD36, CD38, CD45, CD49d, CD50, CD62E, L, S, CD80, CD86, CD95, CD117, CD133, SSEA-1, and ABO. Thus, MSCs may be characterized phenotypically and/or functionally according to their differentiative potential.

MSCs may be harvested from a number of sources including but not limited to bone marrow, blood, periosteum, dermis, umbilical cord blood and/or matrix (e.g., Wharton's Jelly), and placenta. Methods for harvest of MSCs are described in greater detail in the Examples. Reference can also be made to U.S. Pat. No. 5,486,359 for other harvest methods that can be used in the present disclosure.

A fibroblast is a type of cell that synthesizes the extracellular matrix and collagen, the structural framework (e.g., stroma) for animal tissues, and plays a critical role in wound healing. Fibroblasts are the most common cells of connective tissue in animals. Fibroblasts typically have a branched cytoplasm surrounding an elliptical, speckled nucleus having two or more nucleoli. Active fibroblasts can be recognized by their abundant rough endoplasmic reticulum. Inactive fibroblasts, which are also called fibrocytes, are smaller and spindle shaped. They have a reduced rough endoplasmic reticulum.

Sources of fibroblasts include connective tissues such as loose, dense, elastic, reticular, and adipose connective tissue. In addition, there are embryonic connective tissues, as well as specialized connective tissues, which include bone, cartilage, and blood. Other sources include the skin. Methods for isolating and culturing fibroblasts are well known in the art (See, e.g., Weber et al., "Isolation and Culture of Fibroblasts, Vascular Smooth Muscle, and Endothelial Cells From the Fetal Rat Ductus Arteriosus." *Pediatric Research.* 2011; 70, 236-241; Huschtscha et al., "Enhanced isolation of fibroblasts from human skin explants." *Biotechniques.* 2012; 53(4):239-44; the entire contents of which are hereby incorporated by reference).

In some embodiments, fibroblasts, or fibroblast conditioned media, are used for the production and isolation of exosomes as described herein. Methods for producing and isolating exosomes from fibroblasts are known in the art (See, e.g., Luga et al., "Exosomes mediate stromal mobilization of autocrine Wnt-PCP signaling in breast cancer cell migration." *Cell.* 2012; 151(7):1542-56; Bang et al., "Cardiac fibroblast-derived microRNA passenger strand-enriched exosomes mediate cardiomyocyte hypertrophy." *J Clin Invest.* 2014; 124(5):2136-46; Hoffman, "Stromal-cell and cancer-cell exosomes leading the metastatic exodus for the promised niche." *Breast Cancer Research,* 2013; 15:310; the entire contents of each are hereby incorporated by reference.)

A macrophage is a cell produced by the differentiation of monocytes in tissues. Macrophages function in both non-specific defense (innate immunity) as well as help initiate specific defense mechanisms (adaptive immunity) of vertebrate animals. They are specialized phagocytic cells that attack foreign substances, infectious microbes and cancer cells through destruction and ingestion. They are present in all living tissues, and have a function in regeneration. Macrophages can be identified by specific expression of a number of proteins including CD14, CD40, CD11b, CD64, F4/80 (mice)/EMR1 (human), lysozyme M, MAC-1/MAC-3 and CD68 by flow cytometry, immunohistochemical staining, or other suitable methods.

Sources of macrophages include nearly any tissue, and are readily sourced from blood and bone marrow. Methods of isolating and culturing macrophages are well known in the art (See, e.g., Bennet, "Isolation and cultivation in vitro of macrophages from various sources in the mouse." *Am J Pathol.* January 1966; 48(1): 165-181; Davies and Gordon, "Isolation and culture of murine macrophages." *Methods Mol Biol.* 2005; 290:91-103; Weischenfeldt and Porse, "Bone Marrow-Derived Macrophages (BMM): Isolation and Applications." *CSH Protoc.* 2008: pdb.prot5080. doi: 10.1101/pdb.prot5080; the entire contents of each are hereby incorporated by reference.)

In some embodiments, macrophages, or macrophage conditioned media, are used for the production and isolation of exosomes as described herein. Methods for producing and isolating exosomes from macrophages are known in the art (See, e.g., Lee et al., "Exosomes derived from human macrophages suppress endothelial cell migration by controlling integrin trafficking." *Eur J Immunol.* 2014; 44(4):1156-69; Yang et al., "Microvesicles secreted by macrophages shuttle invasion-potentiating microRNAs into breast cancer cells." *Mol Cancer.* 2011; 10:117; Lee et al., "Exosome release of ADAM15 and the functional implications of human macrophage-derived ADAM15 exosomes." *FASEB J.* 2012; 26(7):3084-95; the entire contents of each are hereby incorporated by reference.)

The MSCs, fibroblasts, and/or macrophages, and thus the exosomes derived therefrom, contemplated for use in the methods of the disclosure may be derived from the same subject to be treated (and therefore would be referred to as autologous to the subject) or they may be derived from a different subject preferably of the same species (and therefore would be referred to as allogeneic to the subject).

As used herein, it is to be understood that aspects and embodiments of the disclosure relate to cells as well as cell populations, unless otherwise indicated. Thus, where a cell is recited, it is to be understood that a cell population is also contemplated unless otherwise indicated.

As used herein, an isolated cell (e.g., MSC, fibroblast, and/or macrophage) is a cell that has been physically separated from its natural environment, including physical separation from one or more components of its natural environment. Thus, an isolated cell or cell population embraces a cell or a cell population that has been manipulated in vitro or ex vivo. As an example, isolated cells (e.g., MSCs, fibroblasts, and/or macrophages) may be cells that have been physically separated from at least 50%, preferably at least 60%, more preferably at least 70%, and even more preferably a least 80% of the cells in the tissue from which the cells are harvested. In some instances, the isolated cells are present in a population that is at least 40%, at least 50%, at least 60%, at least 70%, at least 80%, at least 85%, at least 90%, at least 95%, at least 96%, at least 97%, at least 98%, at least 99%, or 100% cells as phenotypically and/or functionally defined herein. Preferably the ratio of MSCs, fibroblasts and/or macrophages to other cells is increased in the isolated preparation as compared to the starting population of cells.

MSCs can be isolated using methods known in the art, e.g., from bone marrow mononuclear cells, umbilical cord blood, adipose tissue, placental tissue, based on their adherence to tissue culture plastic. For example, MSCs can be isolated from commercially available bone marrow aspirates. Enrichment of MSCs within a population of cells can be achieved using methods known in the art including but not limited to FACS.

Commercially available media may be used for the growth, culture and maintenance of MSCs, fibroblasts, and macrophages. Such media include but are not limited to Dulbecco's modified Eagle's medium (DMEM). Components in such media that are useful for the growth, culture and maintenance of MSCs, fibroblasts, and macrophages include but are not limited to amino acids, vitamins, a carbon source (natural and non-natural), salts, sugars, plant derived hydrolysates, sodium pyruvate, surfactants, ammonia, lipids, hormones or growth factors, buffers, non-natural amino acids, sugar precursors, indicators, nucleosides and/or nucleotides, butyrate or organics, DMSO, animal derived products, gene inducers, non-natural sugars, regulators of intracellular pH, betaine or osmoprotectant, trace elements, minerals, non-natural vitamins. Additional components that can be used to supplement a commercially available tissue culture medium include, for example, animal serum (e.g., fetal bovine serum (FBS), fetal calf serum (FCS), horse serum (HS)), antibiotics (e.g., including but not limited to, penicillin, streptomycin, neomycin sulfate, amphotericin B, blasticidin, chloramphenicol, amoxicillin, bacitracin, bleomycin, cephalosporin, chlortetracycline, zeocin, and puromycin), and glutamine (e.g., L-glutamine). Mesenchymal stem cell survival and growth also depends on the maintenance of an appropriate aerobic environment, pH, and temperature. MSCs can be maintained using methods known in the art. (See for example Pittenger et al., Science, 284: 143-147 (1999).)

Certain aspects of the disclosure relate to the unexpected finding that culture conditions can bias the production of exosome type. For example, as described in the Examples, the culture conditions can bias the production of a-type exosomes versus f-type exosomes. In some embodiments, three-dimensional (3D) culturing enhances the production of a-type exosomes over f-type exosomes, as compared to traditional two-dimensional (e.g., monolayer) culturing. Methods for 3D culture are well known in the art, and include, but are not limited to hanging drop culture, culturing on matrices, culturing on microcarriers, culturing on synthetic extracellular scaffolds, culturing on chitosan membranes, culturing under magnetic levitation, suspension culture in rotating bioreactors, or culturing under non-contact inhibition conditions. See, e.g., Haycock J W. (2011). "3D cell culture: a review of current approaches and techniques.". *Methods Mol Biol.* 695: 1-15; Lee, J; Cuddihy M J, Kotov N A. (14 Mar. 2008). *Three-dimensional cell culture matrices: state of the art.* doi:10.1089/teb.2007.0150; Pampaloni, Francesco (October 2007). "The third dimension bridges the gap between cell culture and live tissue". *Nature Reviews* 8: 839-845; and Souza, Glauco (14 Mar. 2010). "Three-dimensional tissue culture based on magnetic cell levitation". *Nature Nanotechnology:* 291-296; the entire content of each are hereby incorporated by reference. Additionally, it was also unexpectedly found that the addition of certain growth factors enhances the production of a-type exosome over f-type exosomes. For example, the addition of more growth factors selected from TGFβ superfamily (TGFβ1, Activins, BMPs, GDFs, GDNFs, Inhibins, Nodal, Lefty, MIS) EGF, PDGF, or FGF can enhance the production of a-type exosomes over f-type exosomes.

In some embodiments, the enhancement (e.g., in the context of 3D culturing and/or growth factor addition) comprises a 1.1-fold, a 1.2-fold, a 1.3-fold, a 1.5-fold, a 1.6-fold, a 1.7-fold, a 1.8-fold, a 1.9-fold, a 2.0-fold, a 2.5-fold, a 3.0-fold, a 3.5-fold, a 4.0-fold, a 4.5-fold, a 5.0-fold, a 5.5-fold, a 6.0-fold, a 6.5-fold, a 7.0-fold, a 7.5-fold, a 8.5-fold, a 9.0-fold, a 9.5-fold, a 10.0-fold, a 12.0-fold, a 15.0-fold, or a 20.0-fold or more increase of a-type exosomes relative to f-type exosomes.

Subjects

The methods of the disclosure may be performed on any subject likely to derive benefit therefrom, including human subjects, agricultural livestock (e.g., cows, pigs, etc.), prized animals (e.g., horses), companion animals (e.g., dogs, cats, etc.), and the like. In various aspects of the disclosure, human subjects are preferred. In some aspect, human subjects and human MSC exosomes are used.

The subjects may be those that have a disease (or condition) described herein amenable to treatment using the exosomes described in this disclosure, or they may be those that are at risk of developing such a disease (or condition). Such subjects include neonates and particularly neonates born at low gestational age. As used herein, a human neonate refers to an human from the time of birth to about 4 weeks of age. As used herein, a human infant refers to a human from about the age of 4 weeks of age to about 3 years of age. As used herein, low gestational age refers to birth (or delivery) that occurs before a normal gestational term for a given species. In humans, a full gestational term is about 40 weeks and may range from 37 weeks to more than 40 weeks. Low gestational age, in humans, akin to a premature birth is defined as birth that occurs before 37 weeks of gestation. The disclosure therefore contemplates prevention and/or treatment of subjects born before 37 weeks of gestation, including those born at even shorter gestational terms (e.g., before 36, before 35, before 34, before 33, before 32, before 31, before 30, before 29, before 28, before 27, before 26, or before 25 weeks of gestation). Typically such premature infants will be treated as neonates, however the disclosure contemplates their treatment even beyond the neonate stage and into childhood and/or adulthood. Certain subjects may have a genetic predisposition to certain forms of the diseases (or conditions) described herein such as for example pulmonary hypertension, and those subjects may also be treated according to the disclosure.

Methods of Preventing and Treating Diseases

The disclosure contemplates preventing and treating certain diseases or disorders. Preventing a disease means reducing the likelihood that the disease manifests itself and/or delaying the onset of the disease. Treating a disease means reducing or eliminating the symptoms of the disease. As described herein, exosomes of the a-type comprise functional signaling components of the TGF/BMP pathway, and are therapeutically effective in the treatment of disorders involving this pathway. Such disorders include certain lung and vascular disorders, as described herein (See, e.g., Cai et al., "BMP signaling in vascular diseases" *FEBS Lett.* 2012 (14): 1993-2002.; Davies et al., "TGF-β/BMP Signaling in Pulmonary Vascular Disease." *Vascular Complications in Human Disease.* Springer, 2008, pp 46-59; Alejandre-Alcázar et al., "Hyperoxia modulates TGF-beta/BMP signaling in a mouse model of bronchopulmonary dysplasia." *Am J Physiol Lung Cell Mol Physiol.* 2007; 292(2):L537-49; Stumm et al., "Lung Remodeling in a Mouse Model of Asthma Involves a Balance between TGF-β1 and BMP-7." *PLoS One.* 2014; DOI: 10.1371/journal.pone.0095959; the entire contents of each are hereby incorporated by reference). Indeed, as demonstrated in the Examples, treatment of mice by I.V. injection of a-type exosome preparations down-regulated the hypoxic activation of signaling associated with vascular remodeling and pulmonary hypertension and ameliorated the hypoxia-induced lung inflammation.

Accordingly, aspects of the disclosure provide compositions and methods to prevent and/or treat a number of lung (or pulmonary) diseases. These diseases include inflammatory lung diseases such as but not limited to pulmonary hypertension (PH) which is also referred to as pulmonary artery hypertension (PAH), asthma, bronchopulmonary dysplasia (BPD), allergies, sarcoidosis, and idiopathic pulmonary fibrosis. These diseases also include lung vascular diseases which may not have an inflammatory component. Still other pulmonary conditions that may be treated according to the disclosure include acute lung injury which may be associated with sepsis or with ventilation. An example of this latter condition is acute respiratory distress syndrome which occurs in older children and adults.

Pulmonary hypertension is a lung disease characterized by blood pressure in the pulmonary artery that is far above normal levels. Symptoms include shortness of breath, chest pain particularly during physical activity, weakness, fatigue, fainting, light headedness particularly during exercise, dizziness, abnormal heart sounds and murmurs, engorgement of the jugular vein, retention of fluid in the abdomen, legs and ankles, and bluish coloring in the nail bed.

Bronchopulmonary dysplasia is a condition that afflicts neonates who have been given oxygen or have been on ventilators, or neonates born prematurely particularly those born very prematurely (e.g., those born before 32 weeks of gestation). It is also referred to as neonatal chronic lung disease. Causes of BPD include mechanical injury for example as a result of ventilation, oxygen toxicity for example as a result of oxygen therapy, and infection. The disease may progress from non-inflammatory to inflammatory with time. Symptoms include bluish skin, chronic cough, rapid breathing, and shortness of breath. Subjects having BPD are more susceptible to infections such as respiratory syncytial virus infection. Subjects having BPD may develop pulmonary hypertension.

Acute respiratory distress syndrome (ARDS), also known as respiratory distress syndrome (RDS) or adult respiratory distress syndrome is a condition that arises as a result of injury to the lungs or acute illness. The injury to the lung may be a result of ventilation, trauma, burns, and/or aspiration. The acute illness may be infectious pneumonia or sepsis. It is considered a severe form of acute lung injury, and it is often fatal. It is characterized by lung inflammation, impaired gas exchange, and release of inflammatory mediators, hypoxemia, and multiple organ failure. ARDS can also be defined as the ratio of arterial partial oxygen tension ($PaO_2$) as a fraction of inspired oxygen ($FiO_2$) below 200 mmHg in the presence of bilateral infiltrates on the chest x-ray. A $PaO_2/FiO_2$ ratio less than 300 mmHg with bilateral infiltrates indicates acute lung injury, which is often a precursor to ARDS. Symptoms of ARDS include shortness of breath, tachypnea, and mental confusion due to low oxygen levels.

Idiopathic pulmonary fibrosis is characterized by scarring or thickening of the lungs without a known cause. It occurs most often in persons 50-70 years of age. Its symptoms include shortness of breath, regular cough (typically a dry cough), chest pain, and decreased activity level.

Allergy is a hypersensitivity disorder of the immune system, with symptoms including red eyes, itchiness, and runny nose, eczema, hives, or an asthma attack. Allergies play a major role in conditions such as asthma. Severe allergies to environmental or dietary allergens or to medication may result in life-threatening reactions called anaphylaxis. Allergic reactions can occur when a person's immune system reacts to what is often a normally harmless substance in the environment. Allergy is one of four forms of hypersensitivity and is sometimes called type I (or immediate) hypersensitivity. Allergic reactions are distinctive because of excessive activation of certain white blood cells (mast cells and basophils) by Immunoglobulin E (IgE). This reaction results in an inflammatory response which can range from mild discomfort to dangerous. A variety of tests exist to diagnose allergic conditions. Tests include placing possible allergens on the skin and looking for a reaction such as swelling and blood tests to look for an allergen-specific IgE.

Hypoxia-induced lung inflammation is a condition often resulting from acute lung injury and/or ARDS, whereby an inflammatory response results from prolonged exposure to hypoxic conditions. Such inflammatory response includes increased macrophages, neutrophils, and inflammatory cytokines, including IL-1β, IL-6, IL-8, and TNF-α, in the bronchoalveolar lavage fluid of humans exposed to hypobaric hypoxia.

Other disorders which are amenable to treatment using the a-type exosomes, e.g., by augmenting the TGF/BMP pathway include cardiovascular disorders, for example myocardial infarction, cardiovascular disease, hypertension, atherosclerosis, and heart failure (See, e.g., Pardali et al., "TGFβ Signaling and Cardiovascular Diseases." *Int J Biol Sci* 2012; 8(2):195-213; Garside et al., "Coordinating Notch, BMP, and TGF-β signaling during heart valve development." *Cell Mol Life Sci.* 2013; 70(16):2899-917; Wang et al., "Bmp Signaling in Congenital Heart Disease: New Developments and Future Directions." *Birth Defects Res A Clin Mol Teratol.* 2011; 91(6): 441-448; Ruiz-Ortega et al., "TGF-beta signaling in vascular fibrosis." *Cardiovasc Res.* 2007; 1; 74(2):196-206; Bujak et al., "The role of TGF-β Signaling in Myocardial Infarction and Cardiac Remodeling." *Cardiovasc Res.* 2007; 74(2): 184-195; Chang et al., "Impact of myocardial infarct proteins and oscillating pressure on the differentiation of mesenchymal stem cells: effect of acute myocardial infarction on stem cell differentiation." *Stem Cells.* 2008; 26(7):1901-12; Koitabashi et al., "Pivotal role of cardiomyocyte TGF-β signaling in the murine pathological response to sustained pressure overload." *J Clin Invest.* 2011; 121(6):2301-2312; and Blann et al., "Serum levels of the TGF-beta receptor are increased in atherosclerosis." *Atherosclerosis.* 1996; 120(1-2):221-6; the entire contents of each are hereby incorporated by reference.)

Myocardial infarction is the medical term for an event commonly known as a heart attack. Myocardial infarction occurs when blood stops flowing properly to part of the heart and the heart muscle is injured due to not receiving enough oxygen. This is usually caused when one of the coronary arteries that supplies blood to the heart develops a blockage due to an unstable buildup of white blood cells, cholesterol and fat. The event is called "acute" if it is sudden and serious. Symptoms of an acute myocardial infarction include sudden chest pain that is felt behind the breast bone and sometimes travels to the left arm or the left side of the neck. Additionally, the individual may have shortness of breath, sweating, nausea, vomiting, abnormal heartbeats, and anxiety. Women experience fewer of these symptoms than men, but usually have shortness of breath, weakness, a feeling of indigestion, and fatigue.

Cardiovascular disease refers to any disease that affects the cardiovascular system, principally cardiac disease, vascular diseases of the brain and kidney, and peripheral arterial disease. The causes of cardiovascular disease are diverse but atherosclerosis and/or hypertension are the most common. In addition, with aging come a number of physiological and morphological changes that alter cardiovascular function and lead to increased risk of cardiovascular disease, even in healthy asymptomatic individuals.

Atherosclerosis is a specific form of arteriosclerosis in which an artery wall thickens as a result of invasion and accumulation of white blood cells and containing both living active WBCs (inflammation) and remnants of dead cells, including cholesterol and triglycerides, eventually calcium and other crystallized materials, within the outer-most and oldest plaque. These changes reduce the elasticity of the artery walls but do not affect blood flow for decades because the artery muscular wall enlarges at the locations of plaque. However, the wall stiffening may eventually increase pulse pressure; widened pulse pressure being one possible result of advanced disease within the major arteries. Symptoms can result from a marked narrowing in the coronary arteries, which are responsible for bringing oxygenated blood to the heart, producing symptoms such as the chest pain of angina and shortness of breath, sweating, nausea, dizziness or light-headedness, breathlessness or palpitations. Marked narrowing of the carotid arteries can also present with symptoms such as a feeling of weakness, not being able to think straight, difficulty speaking, becoming dizzy and difficulty in walking or standing up straight, blurred vision, numbness of the face, arms, and legs, severe headache and losing consciousness. These symptoms are also related to stroke i.e., death of brain cells. Stroke is caused by marked narrowing/closure of arteries going to the brain; lack of adequate of blood supply leads to the death of the cells of the affected tissue. Peripheral arteries, which supply blood to the legs, arms, and pelvis, also experience marked narrowing due to plaque rupture and clots. Symptoms for the marked narrowing are numbness within the arms or legs, as well as pain. Another significant location for the plaque formation are the renal arteries, which would supply blood to the kidneys. Plaque occurrence and accumulation leads to decreased kidney blood flow and chronic kidney disease, which, like all other areas, are typically asymptomatic until late stages.

Hypertension or high blood pressure, sometimes called arterial hypertension, is a chronic medical condition in which the blood pressure in the arteries is elevated. Hypertension is classified as either primary (essential) hypertension or secondary hypertension; about 90-95% of cases are categorized as "primary hypertension" which means high blood pressure with no obvious underlying medical cause. The remaining 5-10% of cases (secondary hypertension) are caused by other conditions that affect the kidneys, arteries, heart or endocrine system. Hypertension puts strain on the heart, leading to hypertensive heart disease and coronary artery disease if not treated. Hypertension is also a major risk factor for stroke, aneurysms of the arteries (e.g. aortic aneurysm), peripheral arterial disease and is a cause of chronic kidney disease. Hypertension is rarely accompanied by any symptoms, and its identification is usually through screening, or when seeking healthcare for an unrelated problem. A proportion of people with high blood pressure report headaches (particularly at the back of the head and in the morning), as well as lightheadedness, vertigo, tinnitus (buzzing or hissing in the ears), altered vision or fainting episodes.

Heart failure, often used to mean chronic heart failure, occurs when the heart is unable to provide sufficient pump action to maintain blood flow to meet the needs of the body. When edema is present in addition to the above it is called congestive heart failure (CHF) or congestive cardiac failure (CCF). Heart failure can cause a number of symptoms including shortness of breath, leg swelling, and exercise intolerance. Common causes of heart failure include myocardial infarction (heart attack) and other forms of coronary artery disease, hypertension, valvular heart disease, and cardiomyopathy. The term heart failure is sometimes incorrectly used for myocardial infarction (which may cause heart failure, but is not heart failure in itself) or for cardiac arrest (in which blood flow effectively stops altogether).

Still other disorders which are amenable to treatment using the a-type exosomes, e.g., by augmenting the TGF/BMP pathway include renal disorders, for example ischemic renal injury, acute renal failure, and renal fibrosis (See, e.g., Meng et al., "Role of the TGF-β/BMP-7/Smad pathways in renal diseases." *Clin Sci (Lond).* 2013; 124(4):243-54; Zerisberg et al., "BMP-7 counteracts TGF-beta1-induced epithelial-to-mesenchymal transition and reverses chronic renal injury." *Nat Med.* 2003; 9(7):964-8; and Yanagita, "Inhibitors/antagonists of TGF-β system in kidney fibrosis." *Neph-* rol Dial Transplant. 2012; 27(10):3686-91; the entire contents of each are hereby incorporated by reference.)

Ischemic renal injury or ischemic nephropathy occurs when there is inadequate blood flow (hypoperfusion) to the kidneys. Hypoperfusion can results in loss of kidney function and kidney atrophy (shrinkage). Renal failure results when this process damages both kidneys. One of the following clinical situations is often present in ischemic nephropathy: bilateral renal artery stenosis (RAS; a narrowing of the large arteries that supply both kidneys); unilateral RAS in a person who has only one functioning kidney; or unilateral RAS with hypertensive (high blood pressure) damage to the other kidney. Symptoms of ischemic renal injury include uremia (high blood levels of protein by-products, such as urea); acute episodes of dyspnea (labored or difficult breathing) caused by sudden accumulation of fluid in the lungs; and hypertension may be present, depending on the severity of the injury. Bruits (sound or murmurs heard with a stethoscope) caused by turbulent blood flow within the arteries may be detected in the neck (carotid artery bruit), abdomen (which may reflect narrowing of the renal artery), and groin (femoral artery bruit).

Acute renal failure or acute kidney injury (AKI), is an abrupt loss of kidney function that typically develops within 7 days. It generally occurs as a result of damage to the kidney tissue caused by decreased renal blood flow (renal ischemia) from any cause (e.g. low blood pressure), exposure to substances harmful to the kidney, an inflammatory process in the kidney, or an obstruction of the urinary tract which impedes the flow of urine. Acute renal failure is diagnosed on the basis of characteristic laboratory findings, such as elevated blood urea nitrogen and creatinine, or inability of the kidneys to produce sufficient amounts of urine. Acute renal failure may lead to a number of complications, including metabolic acidosis, high potassium levels, uremia, changes in body fluid balance, and effects to other organ systems. Symptoms of acute kidney injury include accumulation of urea and other nitrogen-containing substances in the bloodstream lead to a number of symptoms, such as fatigue, loss of appetite, headache, nausea and vomiting. Increases in the potassium level can lead to irregularities in the heartbeat, which can be severe and life-threatening. Fluid balance is often affected, though hypertension is rare. Pain in the flanks is encountered in some conditions (e.g., thrombosis of the renal blood vessels or inflammation of the kidney); this is the result of stretching of the fibrous tissue capsule surrounding the kidney. If the kidney injury is the result of dehydration, there may be thirst as well as evidence of fluid depletion on physical examination. Physical examination may also provide other clues as to the underlying cause of the kidney problem, such as a rash in interstitial nephritis and a palpable bladder. Decreased ability to excrete sufficient fluid from the body can cause accumulation of fluid in the limbs (peripheral edema) and the lungs (pulmonary edema), as well as cardiac tamponade as a result of fluid effusions.

Renal fibrosis results from an excessive accumulation of extracellular matrix that occurs in virtually every type of chronic kidney disease. The pathogenesis of renal fibrosis is a progressive process that typically leads to end-stage renal failure. In some aspects, renal fibrosis represents a failed wound-healing process of the kidney tissue after chronic, sustained injury. Many cellular pathways, e.g., mesangial and fibroblast activation as well as tubular epithelial-mesenchymal transition, have been identified as the major causes for the generation of the matrix-producing cells in diseased conditions. Fibrogenic factors that regulate renal fibrotic process, such as transforming growth factor (TGF), contribute to the condition. Recent discoveries on endogenous antifibrotic factors have evolved novel strategies aimed at antagonizing the fibrogenic action of TGF-/Smad signaling.

Yet other disorders which are amenable to treatment using the a-type exosomes, e.g., by augmenting the TGF/BMP pathway include ischemic neural disorders such as hypoxic ischemic encephalopathy or ischemic stroke (See, e.g., Harvey et al., "Stroke and TGF-beta proteins: glial cell line-derived neurotrophic factor and bone morphogenetic protein." *Pharmacol Ther.* 2005; 105(2):113-25; Krampert et al., "Smad7 regulates the adult neural stem/progenitor cell pool in a transforming growth factor beta- and bone morphogenetic protein-independent manner." *Mol Cell Biol.* 2010; 30(14):3685-94; and Yin et al., "Effect of hyperbaric oxygen on neurological recovery of neonatal rats following hypoxic-ischemic brain damage and its underlying mechanism." *Int J Clin Exp Pathol.* 2013; 6(1): 66-75; the entire content of each are hereby incorporated by reference.)

Hypoxic ischemic encephalopathy (HIE) or perinatal asphyxia, is characterized by clinical and laboratory evidence of acute or sub-acute brain injury due to asphyxia. The primary causes of this condition are systemic hypoxemia and/or reduced cerebral blood flow. Birth asphyxia causes 840,000 or 23% of all neonatal deaths worldwide. Signs and symptoms of mild hypoxic-ischemic encephalopathy include: muscle tone being slightly increased; and transient behavioral abnormalities (such as poor feeding, irritability, or excessive crying or sleepiness) may be observed. Symptoms of moderately severe hypoxic-ischemic encephalopathy include: the infant being lethargic, with significant hypotonia and diminished deep tendon reflexes; the grasping, Moro, and sucking reflexes may be sluggish or absent; the infant may experience occasional periods of apnea; and seizures may occur early within the first 24 hours after birth. Symptoms of severe hypoxic-ischemic encephalopathy include seizures which are delayed and severe and which may be initially resistant to conventional treatments. The seizures are usually generalized, and their frequency may increase during the 24-48 hours after onset, correlating with a phase of reperfusion injury. Other symptoms include: stupor or coma (the infant may not respond to any physical stimulus except the most noxious); irregular breathing; generalized hypotonia and depressed deep tendon reflexes; absent neonatal reflexes (e.g., sucking, swallowing, grasping, Moro); disturbances of ocular motion (e.g., a skewed deviation of the eyes, nystagmus, bobbing); dilated pupils, fixed, or poorly reactive to light; and irregularities of heart rate and blood pressure.

Ischemic stroke is the loss of brain function due to a disturbance in the blood supply to the brain. Ischemia is caused by either blockage of a blood vessel via thrombosis or arterial embolism, or by cerebral hypoperfusion. As a result, the affected area of the brain cannot function normally, which might result in an inability to move one or more limbs on one side of the body, failure to understand or formulate speech, or a vision impairment of one side of the visual field.

Prevention and/or treatment may involve in some instances use of the a-type exosomes alone or together with one or more secondary agents. Subjects may also be subjected to mechanical interventions such as ventilation with or without exogenous oxygen administration.

With respect to neonates and particularly low gestation age neonates, the disclosure contemplates administration of a-type exosomes within 4 weeks, 3 weeks, 2 weeks, 1 week, 6 days, 5 days, 4 days, 3 days, 2 days, 1 day, 12 hours, 6 hours, 3 hours, or 1 hour of birth. In some important instances, the a-type exosomes are administered within 1 hour of birth.

The disclosure further contemplates administration of a-type exosomes even in the absence of symptoms indicative of a disease or disorder as described herein.

The disclosure also contemplates repeated administration of a-type exosomes, including two, three, four, five or more administrations of a-type exosomes. In some instances, the a-type exosomes may be administered continuously. Repeated or continuous administration may occur over a period of several hours (e.g., 1-2, 1-3, 1-6, 1-12, 1-18, or 1-24 hours), several days (e.g., 1-2, 1-3, 1-4, 1-5, 1-6 days, or 1-7 days) or several weeks (e.g., 1-2 weeks, 1-3 weeks, or 1-4 weeks) depending on the severity of the condition being treated. If administration is repeated but not continuous, the time in between administrations may be hours (e.g., 4 hours, 6 hours, or 12 hours), days (e.g., 1 day, 2 days, 3 days, 4 days, 5 days, or 6 days), or weeks (e.g., 1 week, 2 weeks, 3 weeks, or 4 weeks). The time between administrations may be the same or they may differ. As an example, if the symptoms of the disease appear to be worsening the a-type exosomes may be administered more frequently, and then once the symptoms are stabilized or diminishing the a-type exosomes may be administered less frequently.

In some important instances, the a-type exosomes are administered at least once within 24 hours of birth and then at least once more within 1 week of birth. Even more preferably, the a-type exosomes are administered at least once within 1 hour of birth and then at least once more within 3-4 days of birth.

In some instances, repeated intravenous administration of low doses of a-type exosomes may occur. Accordingly, the disclosure contemplates repeated administration of low dosage forms of a-type exosomes as well as single administrations of high dosage forms of a-type exosomes. Low dosage forms may range from, without limitation, 1-50 micrograms per kilogram, while high dosage forms may range from, without limitation, 51-1000 micrograms per kilogram. It will be understood that, depending on the severity of the disease, the health of the subject, and the route of administration, inter alia, the single or repeated administration of low or high dose a-type exosomes are contemplated by the disclosure.

Administration, Pharmaceutical Compositions, Effective Amounts

The a-type exosomes may be used (e.g., administered) in pharmaceutically acceptable preparations (or pharmaceutically acceptable compositions), typically when combined with a pharmaceutically acceptable carrier. Such preparations may routinely contain pharmaceutically acceptable concentrations of salt, buffering agents, preservatives, compatible carriers, and may optionally comprise other (i.e., secondary) therapeutic agents.

A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

Secondary Therapeutic Agents. The exosomes may be administered with one or more secondary therapeutic agents. As used herein, a therapeutic agent refers to any agent which can be used in the prevention, treatment and/or management of a lung disease such as those discussed herein. These include but are not limited to surfactants, inhaled nitric oxide, almitrine bismesylate, immunomodulators, and anti-oxidants. Examples of immunomodulators include steroids and corticosteroids such as but not limited to methylprednisolone. Examples of antioxidants include but are not limited to superoxide dismutase.

Certain secondary therapeutic agents used in the treatment or management of certain lung and vascular diseases including but not limited to pulmonary hypertension include oxygen, anticoagulants such as warfarin (Coumadin); diuretics such as furosemide (Lasix®) or spironalactone (Aldactone®); calcium channel blockers; potassium such as K-dur®; inotropic agents such as digoxin; vasodilators such as nifedipine (Procardia®) or diltiazem (Cardizem®); endothelin receptor antagonists such as bosentan (Tracleer®) and ambrisentan (Letairis®); prostacyclin analogues such as epoprostenol (Flolan®), treprostinil sodium (Remodulin®, Tyvaso®), and iloprost (Ventavis®); and PDE-5 inhibitors such as sildenafil (Revatio®) and tadalafil (Adcirca®).

Surfactants. The a-type exosomes may be administered with pulmonary surfactants. A pulmonary surfactant is a lipoprotein mixture useful in keeping lung airways open (e.g., by preventing adhesion of alveolar walls to each other). Pulmonary surfactants may be comprised of phospholipids such as dipalmitoylphosphatidylcholine (DPPC), phosphotidylcholine (PC), phosphotidylglycerol (PG); cholesterol; and proteins such as SP-A, B, C and D. Pulmonary surfactants may be derived from naturally occurring sources such as bovine or porcine lung tissue. Examples include Alveofact™ (from cow lung lavage), Curosurf™ (from minced pig lung), Infasurf™ (from calf lung lavage), and Survanta™ (from minced cow lung, with additional components including DPPC, palmitic acid, and tripalmitin). Pulmonary surfactants may also be synthetic. Examples include Exosurf™ (comprised of DPPC with hexadecanol and tyloxapol), Pumactant™ or Artificial Lung Expanding Compound (ALEC) (comprised of DPPC and PG), KL-4 (comprised of DPPC, palmitoyl-oleoyl phosphatidylglyercol, palmitic acid, and synthetic peptide that mimics SP-B), Venticute™ (comprised of DPPC, PG, palmitic acid, and recombinant SP-C). Pulmonary surfactants may be obtained from commercial suppliers.

Effective Amounts. The preparations of the disclosure are administered in effective amounts. An effective amount is that amount of an agent that alone stimulates the desired outcome. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

Administration Route. The a-type exosomes may be administered by any route that effects delivery to the lungs or other tissues. Systemic administration routes such as intravenous bolus injection or continuous infusion are suitable. More direct routes such as intranasal administration, intratracheal administration (e.g., via intubation), and inhalation (e.g., via an aerosol through the mouth or nose) are also contemplated by the disclosure and in some instances may be more appropriate particularly where rapid action is necessary. As used herein, an aerosol is a suspension of liquid dispersed as small particles in a gas, and it includes a fine mist or a spray containing such particles. As used herein, aerosolization is the process of producing of an aerosol by transforming a liquid suspension into small particles or droplets. This may be done using an aerosol delivery system such as a pressurized pack or a nebulizer. Nebulizers include air-jet (i.e., pneumatic), ultrasonic, and vibrating-mesh nebulizers, for example with the use of a suitable propellant such as but not limited to dichlorodifluoromethane, trichlorofluoromethane, dichlorotetrafluoroethane, carbon dioxide or other suitable gas. In addition to nebulizers, other devices for pulmonary delivery include but are not limited to metered dose inhalers (MDIs) and dry powder inhalers (DPIs). Capsules and cartridges of for example gelatin for use in an inhaler or insufflator may be formulated containing lyophilized exosomes and a suitable powder base such as lactose or starch.

The exosomes, when it is desirable to deliver them systemically, may be formulated for parenteral administration by injection, including for example by bolus injection or continuous infusion. Formulations for injection may be presented in unit dosage form, e.g., in ampoules or in multi-dose containers, with or without an added preservative.

The compositions may take such forms as water-soluble suspensions, solutions or emulsions in oily or aqueous vehicles, and may contain formulatory agents such as suspending, stabilizing and/or dispersing agents. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase solubility. Alternatively, the exosomes may be in lyophilized or other powder or solid form for constitution with a suitable vehicle, e.g., sterile pyrogen-free water, before use.

It is to be understood that other agents to be administered to subjects being treated according to the disclosure may be administered by any suitable route including oral administration, intranasal administration, intratracheal administration, inhalation, intravenous administration, etc. Those of ordinary skill in the art will know the customary routes of administration for such secondary agents.

Kits

The disclosure also encompasses a packaged and labelled pharmaceutical product. This article of manufacture or kit includes the appropriate unit dosage form in an appropriate vessel or container such as a glass vial or plastic ampoule or other container that is hermetically sealed. The unit dosage form should be suitable for pulmonary delivery for example by aerosol. Preferably, the article of manufacture or kit further comprises instructions on how to use including how to administer the pharmaceutical product. The instructions may further contain informational material that advises a medical practitioner, technician or subject on how to appropriately prevent or treat the disease or disorder in question. In other words, the article of manufacture includes instructions indicating or suggesting a dosing regimen for use including but not limited to actual doses, monitoring procedures, and other monitoring information.

As with any pharmaceutical product, the packaging material and container are designed to protect the stability of the product during storage and shipment.

The kits may include exosomes in sterile aqueous suspensions that may be used directly or may be diluted with normal saline for intravenous injection or use in a nebulizer, or dilution or combination with surfactant for intratracheal administration. The kits may therefore also contain the diluent solution or agent, such as saline or surfactant. The kit may also include a pulmonary delivery device such as a nebulizer or disposable components therefore such as the mouthpiece, nosepiece, or mask.

EXAMPLES

Materials and Methods

Isolation of human MSCs from human umbilical cord Wharton's Jelly. Human umbilical cord Wharton's jelly derived MSCs (hUC-MSCs) were isolated according to published methods (Mitchell, K. E. et al., 2003, *Stem Cells* 21:50-60; and Penolazzi, L. et al., 2011, *J Cell Physiol*) with minor modifications. Cord was rinsed twice with cold sterile PBS, cut longitudinally, and arteries and vein were removed. The soft gel tissues were scraped out, finely chopped (2-3 mm$^2$) and directly placed on 100 mm dishes (15 pieces per dish) with DMEM/F12 (1:1) (Invitrogen) supplemented with 10% fetal bovine serum (Hyclone), 2 mM L-glutamine, and penicillin/streptomycin, and incubated for 5 days at 37° C. in a humidified atmosphere of 5% $CO_2$. After removal of tissue and medium, the plates were washed 3 times with PBS, the attached cells were cultured and fresh media replaced 3 times per week. At 70-80% confluence, cells were collected and stained with PE conjugated antibodies for CD34 (Miltenybiotec) and CD45 (Miltenybiotec). Immunodepletion was performed using the anti-PE-microbeads (Miltenybiotec) and MSCS column (Miltenybiotec) according to manufacturer's instructions. The CD34 and CD45 negative populations were further propagated and selected for the expression of MSC markers (CD105, CD90, CD44, and CD73) and the absence of CD11b, CD19, and HLA-DR by using a set of fluorescently-labeled antibodies specific for the characterization of human MSCs (BD Biosciences) using a MoFlo flow cytometry (Beckman Coulter).

Preparation of conditioned media. To exclude contamination from serum-derived microvesicles, serum used for propagation of cell cultures and the collection of conditioned media was clarified by ultracentrifugation at 100,000×g for 18 hrs. MSCs were cultured in α-MEM media supplemented with 10% (v/v) fetal bovine serum (FBS, Hyclone), 10% (v/v) Horse Serum (Hyclone) and 5 mM L-glutamine (Gibco). Cultures at 70% confluence were washed twice with PBS and incubated with serum-free media supplemented with 2 mM L-glutamine for 24 hours under standard culture conditions. Conditioned media were collected from nearly confluent cultures of human MSCs over 24-48 hours or over a period of 3-4 days (in microparticle-depleted FBS cultures) and cells and debris were removed by differential centrifugations at 400×g for 5 min, at 2,000×g for 10 min, and at 13,000×g for 30 min. The clarified conditioned media were subsequently filtered through a 0.2 μm filter unit and concentrated at least 10-fold using a tangential flow filtration system using 100 kD or 300 kD or 500 kD cutoff. Protein levels in the conditioned media were determined by Bradford assay (Bio-Rad).

Isolation of exosomes. MSC exosomes were isolated from the concentrated conditioned media by banding on a 10%-60% step gradient of Iodixanol by centrifugation at 100 k×g for 3.5 hours. Exosomes were further isolated from the conditioned media by differential centrifugation, occasionally followed by a 30% sucrose cushion or sucrose velocity gradients. The particle number of isolated exosome preparations was determined by Nanosight.

Western Blot of exosomes Exosome preparations were separated on 12% polyacrylamide gel and then transferred onto 0.45 µm PVDF membrane (Millipore). Goat polyclonal anti-CD63 (1:1,000; Santa Cruz) antibody, polyclonal rabbit anti-CD81 (1:1,000, Santa Cruz), and monoclonal anti-Dicer (1:1,000, Abcam) were used. Primary antibodies against ALIX, FLOT-1, TSG101, TGFβR2, SMAD, CD105, CD9, CD81, CAV1, EFGR and AKT were also used to identify subpopulations of exosomes. Peroxidase-conjugated anti-rabbit secondary antibody (Santa Cruz) was used in 1:20,000 dilution to visualize immunoreactive bands either by the enhanced chemiluminescence reagent (Pierce) or Lumi-LightPLUS (Roche). The ImageJ program from NIH was used for quantitation through densitometric analysis after appropriate background subtraction.

Quantification of microRNAs. Total exosome RNA was extracted by the method of Chomczynski & Sacchi (1987 *Anal Biochem* 162:156-159) and 750 ng was used as a template for reverse transcriptase with specific primers for each target microRNA (TaqMan Reverse Transcription Kit, Applied Biosystems, Foster City, Calif.). Each reverse transcription reaction included also the primer for the small nuclear RNA sno202, which was used as an internal control. 37.5 ng cDNA was used for each 20 µl qPCR reaction with TaqMan universal master mix II with no UNG (Applied Biosystems) in the presence of probes specific for the indicated microRNAs and the internal control (TaqMan microRNA assay, Applied Biosystems). Amplification was performed at 50° C. for 2 min, 95° C. for 10 min, followed by 40 cycles of 95° C. for 15 sec, 60° C. for 1 min, on a StepOne Plus platform (Applied Biosystems).

Animals and hypoxic exposure. 8-week-old FVB male mice were either obtained from Charles River Laboratories (Wilmington, Mass.) or were raised in the Animal Facility at Children's Hospital Boston. Mice in each group were exposed to 8.5% oxygen in a Plexiglas chamber (OxyCycler, BioSpherix, Redfield, N.Y.) for variable experimental periods. Ventilation was adjusted to remove $CO_2$ so that it did not exceed 5,000 ppm (0.5%) (average range 1,000-3,000 ppm). Ammonia was removed by ventilation and activated charcoal filtration through an air purifier. All animal protocols were approved by the Children's Hospital Animal Care and Use Committee.

Example 1

Identification and Characterization of Two Distinct Populations of Mesenchymal Stem Cell-Derived Exosomes Accumulated evidence supports a critical role for MSCs in lung homeostasis and repair. It has been previously reported that MSC exosomes (MEX) mediate the cytoprotective effect of mesenchymal stem cells on hypoxia-induced pulmonary hypertension. Intravenous mouse MEX delivery suppressed the hypoxic pulmonary influx of macrophages and the induction of pro-inflammatory and pro-proliferative mediators and eventually inhibited vascular remodeling and hypoxic pulmonary hypertension in a murine PH model.

The goal of this study was to investigate whether MSCs isolated from human umbilical cord stroma secrete microvesicles exhibiting similar protective properties, and to characterize the biochemical properties of the therapeutic MSC exosome and study its effect on the vascular cell phenotypic changes triggered by the signals that initiate lung vascular remodeling.

Isolation of MEX

Exosomes (MEX) were isolated from tissue culture media conditioned by human mesenchymal stem cells (MSCs). Here, the source of human MSCs is Wharton's jelly (WJ), although other possible sources are umbilical cord blood, bone marrow, adipose or other tissues. MSCs were isolated, immunoselected, cultured and their differentiation potential assessed. Negative selections for human WJ-MSCs included CD34 and CD45. MSCs were positive for CD90, CD73, CD105 and CD44.

Treatment of Mice with MEX

One dose of MEX was delivered to animals through tail veil injection and recipient mice were exposed to normobaric hypoxia (8-10% O2) for 2.5 days. A decrease in hypoxia-induced inflammatory markers (for example CCL2, IL6), was used as a metric for the effectiveness of the preparation. The dosage used was equivalent to approximately 10-20 billion particles as measured by NanoSight or approximately equivalent to total exosomes produced by 10-20 million MSCs in monolayer cultures over 24 hrs.

Results

Figure 1B:
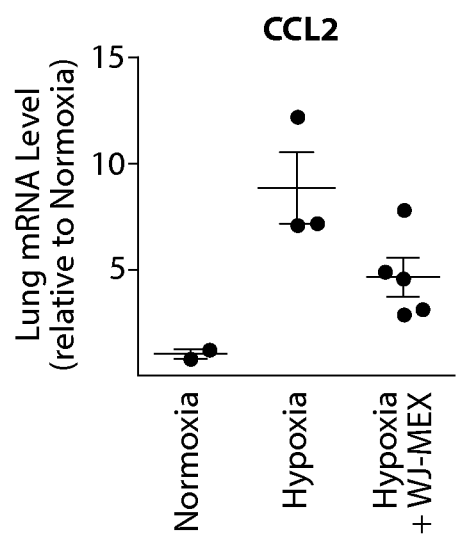

Treatment of mice by I.V. injection of MEX preparations down-regulated the hypoxic activation of signaling associated with vascular remodeling & pulmonary hypertension (FIG. 1A) and ameliorated the hypoxia-induced lung inflammation (FIG. 1B). FIG. 1A shows hypoxia-induced phosphorylation of AKT and its downstream target mTOR are reduced by WJ-MEX treatment. As demonstrated in FIG. 1B, lung protein levels of the Inhibitor of DNA-binding/differentiation protein ID1, a direct SMAD-targeted gene and downstream signal of BMPR2, are suppressed by hypoxia but increased with MEX. Alpha tubulin serves as normalizing control.

Figure 2:
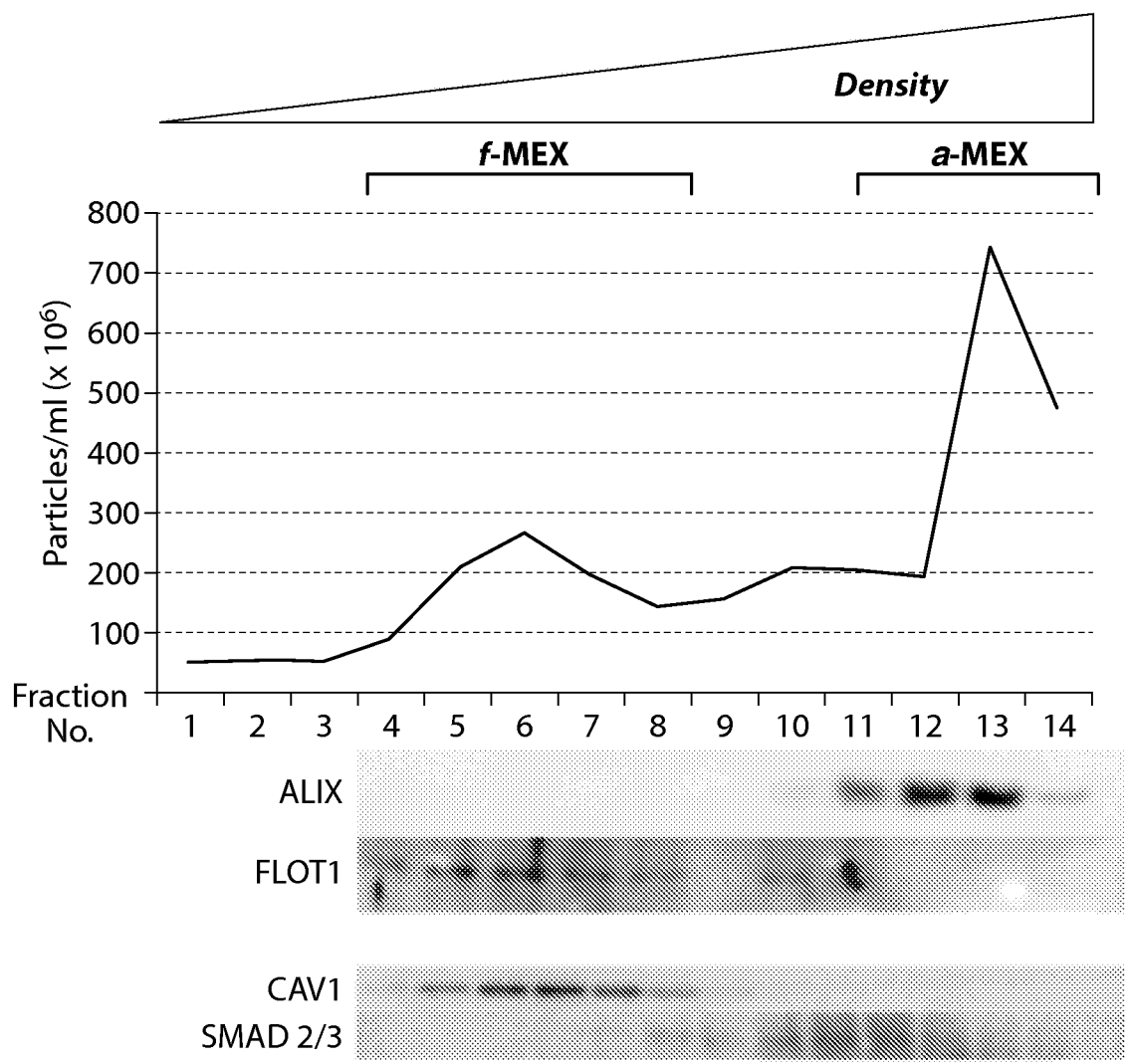
FIG. 2. Isolation of exosome subpopulations enriched for a-MEX and f-MEX. Media conditioned by monolayer cultures of WJ-MSC were concentrated and adjusted to 45% sucrose. This prep was layered on a 60% sucrose cushion and overlayered with a step gradient of 35%-5% sucrose. Preparations were centrifuged for 20 hrs at 180 k×g. The gradient was collected in 14×1 ml fractions. Particle number in each fraction was measured by Nanosight. 20 microL from each fraction were analyzed by Western for the presence of ALIX, FLOT1, CAV1 and SMAD 2/3. Two distinct populations of vesicles were identified with different sedimentation velocities (f-MEX and a-MEX) and different marker composition, based on the above markers.
Figure 3:
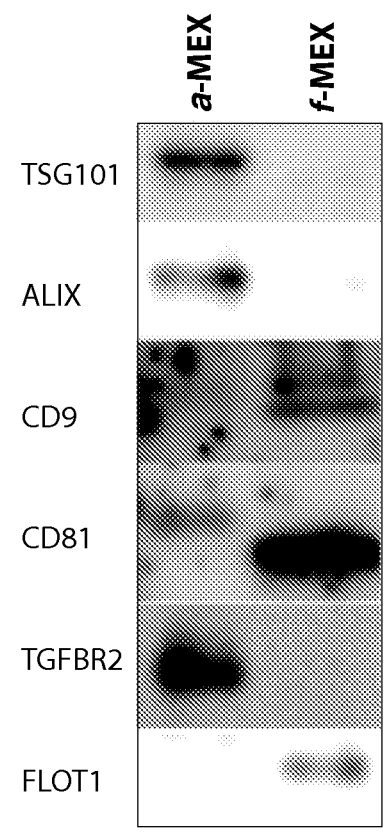
FIG. 3. WJ-MSC preparations representing a-MEX and f-MEX were analyzed by western blotting. Exosome biogenesis markers, such as Alix and Tsg101 are preferentially enriched in a-MEX, while tetraspanins CD9 and CD81 and lipid raft markers, such as flotilin1 and caveolin1 are enriched f-MEX. Also specific for a-MEX are TGFBR2 as well as CD105 and members of the SMAD family (not shown here). EGF Receptor and members of the AKT family (not shown here) are specific to f-MEX.

The presence of more than one population of MEX subtype was investigated by density and velocity ultracentrifugation. Analysis of the MEX preparations through density and velocity ultracentrifugation revealed that the population of extracellular microvesicles produced by MSCs is composed by two types, based on molecular markers (FIG. 2 & FIG. 3). The two types have been termed a-MEX and f-MEX. Exosome biogenesis markers, such as ALIX and TSG101 are preferentially enriched in fractions 12-14 (a-MEX), while tetraspanins CD9 and CD81 and lipid raft markers, such as flotilin1 (FLOT1) and caveolin1 (CAV1) are enriched in fractions 5-8 (f-MEX). Table 1 shows the a-MEX and f-MEX specific markers:

TABLE 1

| a-MEX specific markers | f-MEX specific markers |
|---|---|
| ALIX | FLOT1 |
| TSG101 | CD9 |
| TGFβR2 | CD81 |
| SMADs (1, 2, 3, 5) | CAV1 |
| CD105 | EFGR |
|  | AKT (2, 3) |

Figure 4:
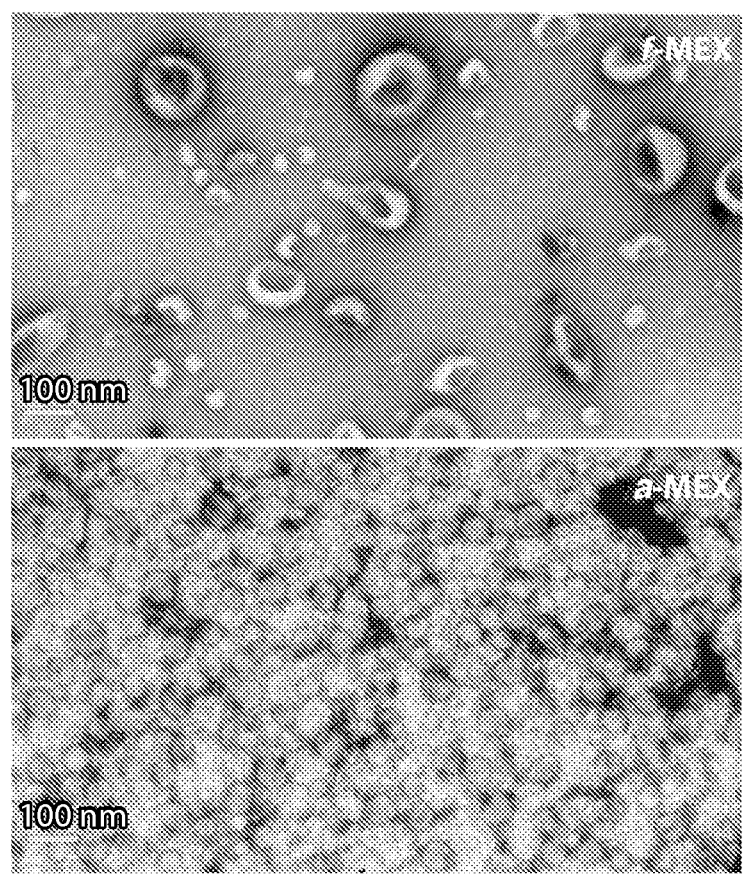
FIG. 4. Negative staining electron microscopy shows differences in size, shape and radiolucency between a-MEX and f-MEX exosome subpopulations. Magnification: 30,000×.

Preparations of a-MEX or f-MEX reveal distinct morphology by EM (FIG. 4). f-MEX are 30-200 nm in diameter and exhibit typical deep cup shape morphology of exosomes, whereas a-MEX are 30-100 nm, with a translucent and spherical morphology.

To prepare exosome subpopulations highly enriched in a-MEX or f-MEX from bulk exosome preparations obtained from MSC grown in monolayer cultures, the bulk exosome preparations were adjusted to 45% sucrose, layered on a 60% sucrose cushion and overlayered with a step gradient of 35%-5% sucrose. Preparations were centrifuged for 20 hrs at 180 k×g to separate a-MEX and f-MEX subpopulations. Gradient fractions containing a-MEX or f-MEX were concentrated though ultracentrifugation (100 k×g, 3 hrs) and resuspended in PBS or though tangential flow filtration.

Figure 5:
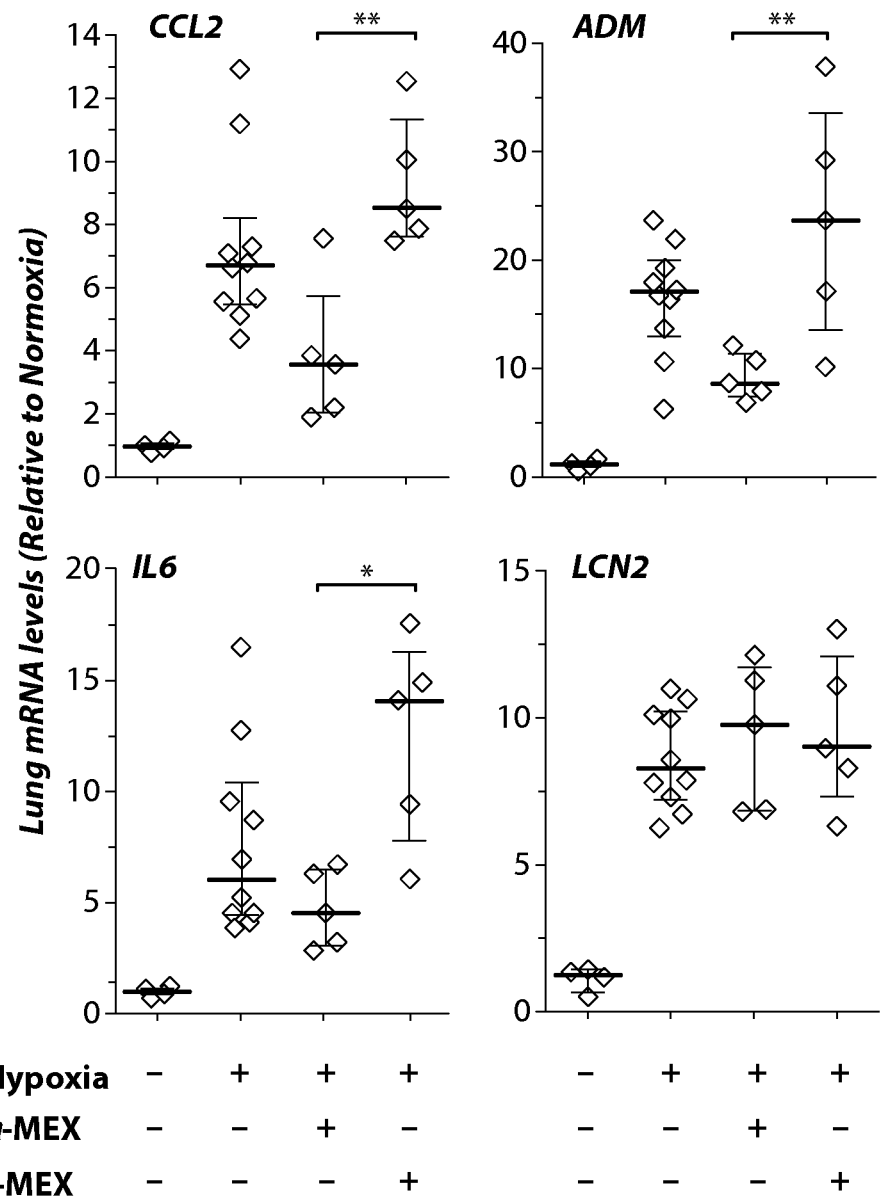
FIG. 5. FVB/n mice were exposed to hypoxia as in FIG. 1 and treated with WJ-MSC exosome preparations enriched in either a-MEX or f-MEX. Lungs were harvested after 2.5 days in hypoxia and the mRNA levels of hypoxia-induced inflammatory markers were determined by RT-PCR, using RPS9 as a normalizer. Treatment with a-MEX but not f-MEX results in decrease in mRNA levels of CCL2, IL6 and ADM.

Administration of isolated a-MEX or f-MEX to mice exposed to hypoxia revealed that the immunosuppressive properties of MEX reside exclusively with the a-MEX type (FIG. 5). Treatment with a-MEX caused a significant decrease in the mRNA levels of hypoxia-induced inflammatory markers, including CCL2, IL6 and ADM.

Production of a-MEX is Augmented in 3-D Cultures

Figure 6:
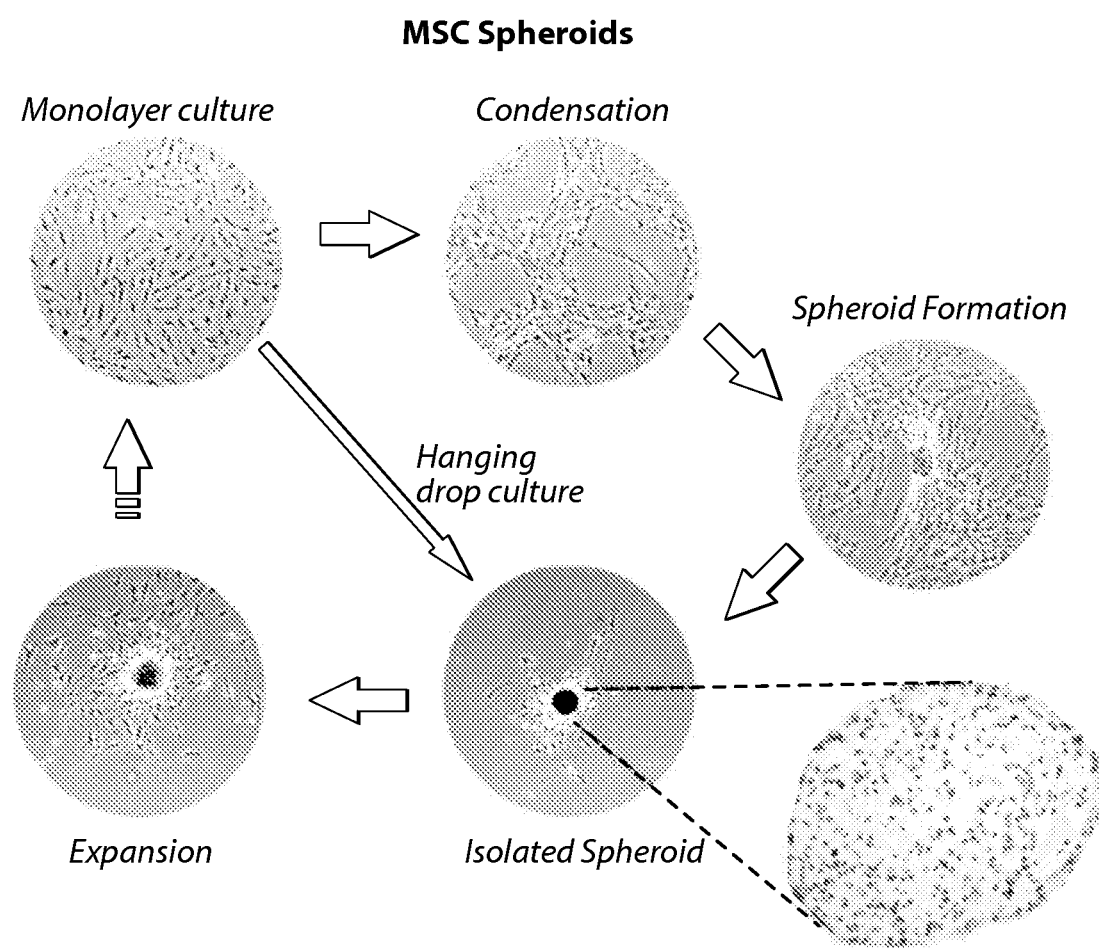
FIG. 6. A schematic of the process of spheroid formation. Addition of TGFβb (10 ng/ml) to monolayer cultures accelerates spheroid formation. The insert represents a section of a spheroid of WJ-MSCs stained with toluidine blue.

MSCs and certain other cell types can form cell aggregates termed spheroids. FIG. 6 presents microscopy images depicting the formation of MSC spheroids from both 2-D and 3D culture conditions. Spheroid formation is assumed to represent more physiological conditions than the 2-dimensional monolayer cultures. For MSCs, the spheroid state is assumed to represent the more undifferentiated stem-like state. 3-dimensional culture systems that enhance the tendency to form spheroids are commercially available (specific membranes). MSCs will spontaneously form spheroids outgrowing from monolayer cultures at high density, and can be induced to form spheroids if suspended in culture media (hanging drop technique).

The hanging drop technique is a well-known method of culture for many cell types. Briefly, MSCs grown in monolayer culture were trypsinized to produce a single cell suspension. 30 μL of this suspension containing 500,000 cells was applied to the inside surface of a petri dish cover and the cover was placed over a dish containing a small amount of PBS to preserve humidity. The dish with the hanging droplets was placed into a tissue culture incubator for 1-2 days, during which time MSCs aggregated into spheroids. A typical spheroid preparation consisted of 15 million cells divided into 30 droplets.

Figure 7:
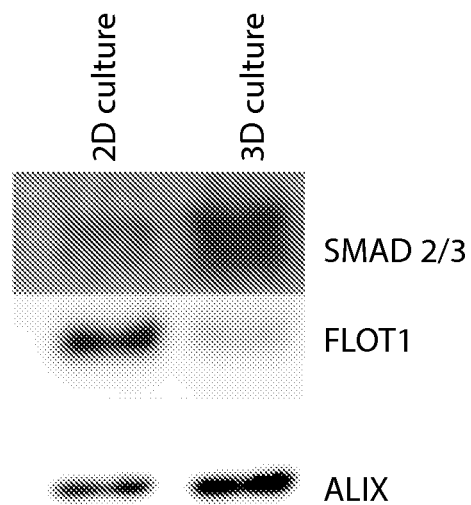
FIG. 7. WJ-MSC spheroids predominantly secrete a-MEX. WJ-MSCs in standard monolayer culture were trypsinized and the single cell suspension was divided in two equal parts, containing 15 million cells each. One part was propagated in standard media and vessel as a monolayer (2D Culture). The other part was induced into spheroid formation (3D culture) by the hanging drop method (30 spheroids containing 500,000 cells each). An equal volume of clarified media conditioned by the two cultures was assayed for the presence of the indicated markers by Western blotting. Markers specific for a-MEX (SMAD 2/3, ALIX) are enriched in media conditioned by spheroids, and FLOT1, specific for f-MEX is observed predominantly in media conditioned by the monolayer.

The data indicate that MSCs grown in 3D culture (spheroids) produce significantly more a-MEX compared with the same MSC clone, at the same passage, grown in 2D culture (monolayer) (FIG. 7). The increase in a-MEX production is evidenced by the strong immunoreactivity of samples to SMAD 2/3 and ALIX antibodies but not FLOT1, as shown in FIG. 7.

Figure 8A:
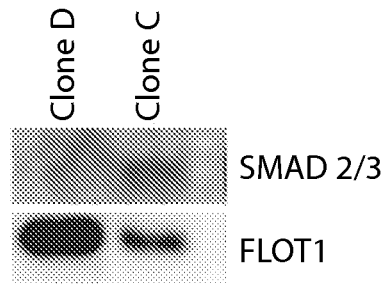
FIG. 8. The f-MEX to a-MEX ratio secreted by MSCs from independent donors is inversely correlated with spheroid-forming efficiency. WJ-MSCs isolated from two different donors (clone D and Clone C) were cultured under non-adherent conditions (hanging drop technique) for 24 h. (A) An equal amount of media conditioned by monolayer cultures of each clone was assayed for the a-MEX marker SMAD 2/3 and the f-MEX marker FLOT1 by western blot. The SMAD vs FLOT1 ratio indicated that clone D produces predominately f-MEX, whereas exosome production of clone C includes significant amounts of both a-MEX and f-MEX. (B) Single cell suspensions of Clone D did not exhibit spheroid forming ability under conditions where identically treated suspensions of Clone C WJ-MSCs were able to form compact spheroids after 24 h as examined by light microscopy. Viability was above 95% after 24 h as assessed by trypan blue. Conditioned media were collected from the hanging drops and exosomes where isolated (as described in Methods). Clone A exosomes were enriched in flotilin1 while clone B in Alix, reflecting differential enrichment of exosome subpopulations in CM.
Figure 8B:
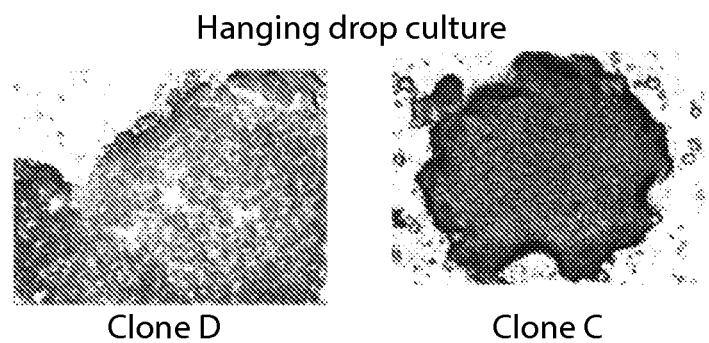

It was also found that production of a-MEX is variable between different MSC clones, and the producing cells can be enriched through 3D culture and/or growth factor supplementation. Various independently derived MSC clones were characterized for their relative a-MEX production (determined the ratio of FLOT1 vs ALIX (or SMAD) markers in their conditioned media during 2D culture and noticed substantial variation) (FIG. 8A). Certain clones, such as Clone D did not produce significant amounts of SMAD (a-MEX marker compared to FLOT1 (f-MEX marker)). This property of Clone D is associated with a very inefficient spheroid formation using the hanging drop technique (FIG. 8B).

Figure 9:
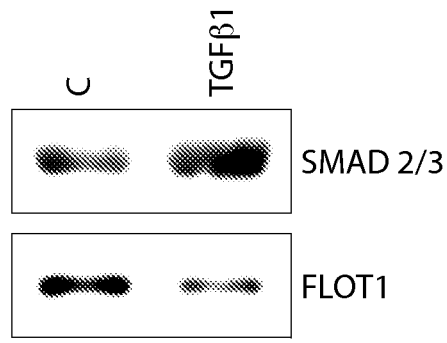
FIG. 9. Addition of TGFβ (10 ng/ml) to monolayer cultures of WJ-MSCs accelerates the process of spheroid formation and results in an increase of the ratio of a-MEX markers (such as SMAD2/3) to f-MEX markers (such as FLOT1), indicating an increased proportion of a-MEX in the secreted population.
Figure 10A:
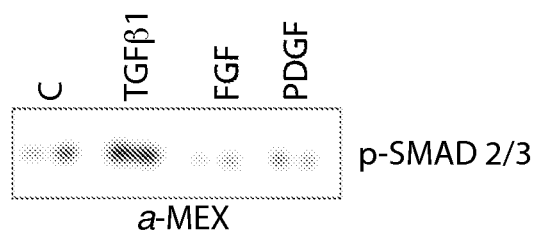
FIG. 10. a-MEX harbor functional modules of TGF signaling. (A) PBS "C", TGFβ, FGF or PDGF (10 ng/ml), was added to equal aliquots of a-MEX preparations, followed by incubation at 37 C for 30 min. The preparations were then lysed and subjected to analysis by western blotting. Increased phosphorylation of exosome-associated SMAD 2/3 indicates a functional TGFB2R receptor complex. The effect is not observed by treatment with FGF or PDGF, growth factors not employing the SMAD pathway in their primary signaling. (B) a-MEX or f-MEX preparations were treated with TGFβ (10 ng/ml) and incubated and analyzed as above. SMAD phosphorylation was specifically observed in a-MEX.
Figure 10B:
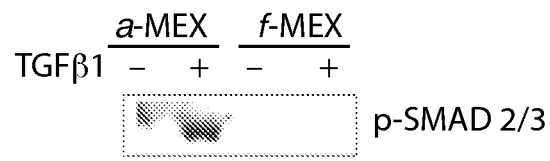

Significantly, when rare spheroids formed by Clone D cells were expanded in monolayer, the resultant 2D-culture produced a-MEX in a high ratio, and formed spheroids with high efficiency. These observations indicate that selection through spheroid formation can be used as a tool to enrich inefficient MSC clones for the subpopulation of cells retaining their stemness and producing a-MEX at high ratios. Towards this goal it was observed that manipulation of the concentrations of growth factors such as TGFβ1 can both accelerate spheroid formation and enhance a-MEX production (FIG. 9). TGFβ1 stimulation was achieved at a concentration of 10 ng/ml.

a-MEX and f-MEX Carry Distinct Signal Transduction Modules for Specific Growth Factors.

a-MEX harbor the TGF receptor and the downstream transcription factor SMAD (FIG. 2 & FIG. 3). Addition of TGFβ1 to isolated preparations of a-MEX reveals that the signaling module is functional, since the SMAD molecule within the a-MEX is efficiently and specifically phosphorylated in vitro (FIG. 10A). This property is specific for a-MEX (FIG. 10B). f-MEX contain the EGF receptor and can phosphorylate endogenous AKT in vitro (not shown).

The data indicate that MSCs produce two different types of exosomes: the a-MEX type carries functional signaling modules for the TGF/BMP superfamily of growth factors, whereas the f-MEX carry the corresponding modules for the FGF/PDGF superfamily. These exosomes transfer the modules to target cells and enhance the corresponding signaling pathway, and their relative secretion ratio depends on the programming of the MSC population producing them.

Figure 11A:
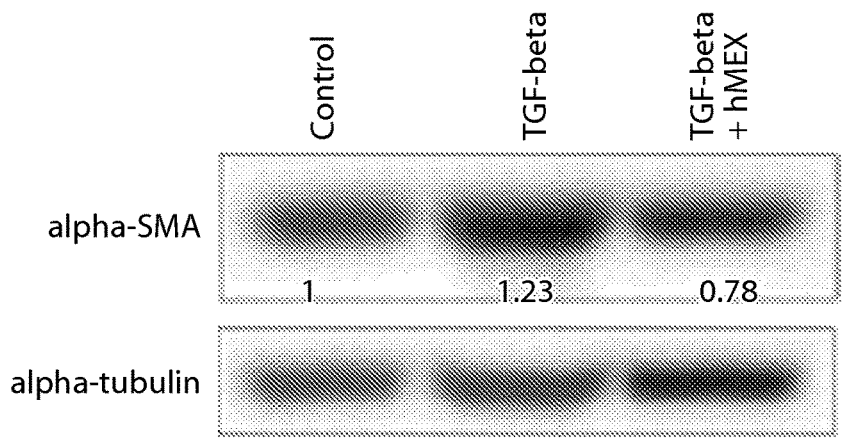
FIG. 11. a-MEX but not f-MEX inhibit the TGFβ-induced fibroblast to myofibroblast transition and the LPS-mediated fibroblast activation. (A) Human lung fibroblasts, after 3 days serum starvation (0.1% FBS), were stimulated with TGFβ to undergo myofibroblast differentiation, marked by increased alpha-smooth muscle actin (SMA) expression. Pretreatment with hMEX (2 ug/ml) abrogates the effect of TGFβ on alpha-SMA protein levels. (B) Human lung fibroblasts, after 24 h serum starvation were stimulated with TGFβ to induce PAI1, a myofibroblast marker. Treatment with a-MEX prevented PAI1 upregulation, an effect not observed with f-MEX treatment. (C) a-MEX treatment down regulates baseline MCP-1 and IL1βmRNA levels in human lung fibroblasts in vitro.
Figure 11B:
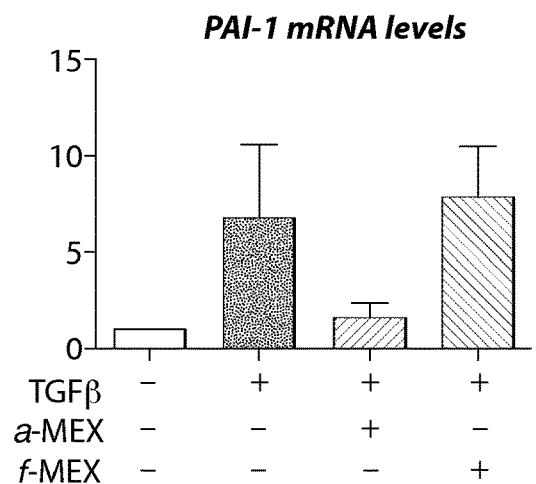
Figure 11C:
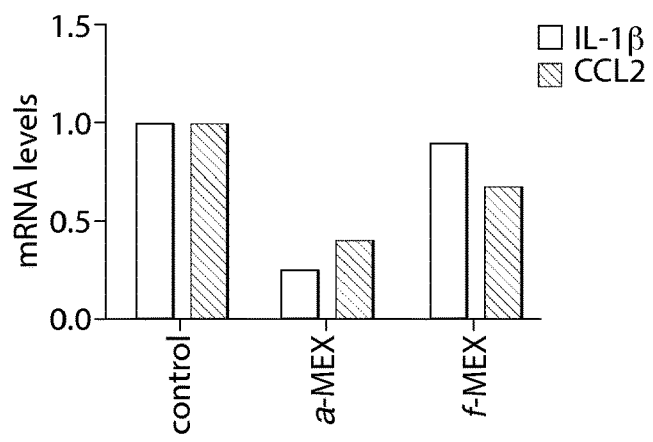

Furthermore, it was found that a-MEX but not f-MEX are able to inhibit the TGFβ-induced fibroblast to myofibroblast transition in human lung cells, as shown in FIG. 11. Human lung fibroblasts, after 3 days serum starvation (0.1% FBS), were stimulated with TGFβ to undergo myofibroblast differentiation, marked by increased alpha-smooth muscle actin (SMA) expression. FIG. 11A demonstrates that pretreatment with hMEX (2 ug/ml) abrogates the effect of TGFβ on alpha-SMA protein levels. To further examine this finding, human lung fibroblasts, after 24 h serum starvation were stimulated with TGFβ to induce PAI1, a myofibroblast marker. Treatment with a-MEX prevented PAI1 up-regulation, an effect not observed with f-MEX treatment (FIG. 11B). It was also found that a-MEX treatment down-regulates baseline MCP-1 and IL1β mRNA levels in human lung fibroblasts in vitro (FIG. 11C).

EQUIVALENTS

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A pharmaceutical composition comprising an isolated exosome, wherein
   (i) the isolated exosome comprises three or more expression markers selected from the group consisting of ALIX, TSG101, TGFBR2, SMAD1, SMAD2, SMAD3, SMAD5 and CD105; and
   (ii) the isolated exosome does not comprise one or more expression markers selected from the group consisting of FLOT1, CD9, CD81, CAV1, EGFR, AKT1 and AKT2,
   and wherein the composition is formulated as an aerosol, a lyophilized powder, or an emulsion.

2. The composition of claim 1, wherein the exosome comprises the expression markers ALIX, TSG101, TGFBR2, SMAD1, SMAD2, SMAD3, SMAD5 and CD105.

3. The composition of claim 1, wherein the exosome does not comprise the expression markers FLOT1, CD9, CD81, CAV1, EGFR, AKT1 and AKT2.

4. The composition of claim 1, wherein the exosome has a diameter in the range of about 10-150 nm.

5. The composition of claim 1, wherein the exosome is isolated from a mesenchymal stem cell (MSC), fibroblast, or macrophage.

6. The composition of claim 5, wherein the MSC, fibroblast, or macrophage is a human MSC, human fibroblast, or human macrophage.

7. The composition of claim 6, wherein the human MSC is isolated from Wharton's jelly, umbilical cord blood, placenta, peripheral blood, bone marrow, or adipose tissue.

8. The composition of claim 1, wherein the composition is formulated as an aerosol.

9. The composition of claim 8, wherein the aerosol is in an aerosol delivery system selected from a nebulizer and an inhaler.

10. The composition of claim 1, wherein the composition is formulated as an lyophilized powder.

11. The composition of claim 10, wherein the lyophilized powder is in a capsule or a cartridge.

12. The composition of claim 1, wherein the composition is formulated as an emulsion.

13. The composition of claim 12, wherein the emulsion comprises the isolated exosome formulated in an oily or aqueous vehicle.

14. The composition of claim 1, wherein the composition is formulated in unit dose form.

* * * * *